US008715161B2

(12) United States Patent
McGough

(10) Patent No.: US 8,715,161 B2
(45) Date of Patent: May 6, 2014

(54) METHOD AND DEVICE FOR FEMALE THERAPEUTIC MASSAGE

(75) Inventor: Paul Stephen McGough, Carolina Beach, NC (US)

(73) Assignee: Human Innovations, LLC, Carolina Beach, NC (US)

( * ) Notice: Subject to any disclaimer, the term of this patent is extended or adjusted under 35 U.S.C. 154(b) by 624 days.

(21) Appl. No.: 13/017,025

(22) Filed: Jan. 30, 2011

(65) Prior Publication Data

US 2011/0190575 A1 Aug. 4, 2011

Related U.S. Application Data

(60) Provisional application No. 61/295,683, filed on Feb. 1, 2010.

(51) Int. Cl.
*A61F 5/00* (2006.01)

(52) U.S. Cl.
USPC .......................................................... 600/38

(58) Field of Classification Search
CPC ....... A61H 19/00; A61H 19/34; A61H 19/44; A61H 23/0254; A61H 2201/0153; A61H 2201/0165; A61H 2201/0192; A61H 2201/1238; A61H 2201/1436; A61H 2201/1623; A61H 2201/1628; A61H 2201/1633; A61H 2205/083; A61H 2205/087
USPC ............. 600/38–41; 601/107, 108, 110, 111, 601/115, 116, 86, 90, 98, 66
See application file for complete search history.

(56) References Cited

U.S. PATENT DOCUMENTS

| | | | | |
|---|---|---|---|---|
| 3,103,925 | A | 9/1963 | Vogt | |
| 3,424,149 | A * | 1/1969 | Fujimoto | 601/111 |
| 4,016,873 | A | 4/1977 | Anderson | |
| 4,069,816 | A | 1/1978 | Yamamura | |
| 6,152,929 | A | 11/2000 | O'Brien | |
| 6,422,993 | B1 | 7/2002 | Hudson | |
| 6,464,653 | B1 | 10/2002 | Hovland | |
| 6,585,668 | B2 * | 7/2003 | Nissim | 601/84 |
| 6,949,067 | B1 | 9/2005 | Dann | |
| 6,981,954 | B2 | 1/2006 | Huang | |
| 7,025,736 | B1 | 4/2006 | Lawrence | |
| 7,056,281 | B2 | 6/2006 | Bookwalter | |
| 7,175,592 | B2 | 2/2007 | Lee | |
| 7,246,781 | B2 | 7/2007 | Nam | |
| 2005/0113636 | A1 | 5/2005 | Tucker | |
| 2011/0264019 | A1 * | 10/2011 | Park | 601/108 |

* cited by examiner

*Primary Examiner* — Samuel Gilbert

(74) *Attorney, Agent, or Firm* — Ariel S. Bentolila; Bay Area IP Group, LLC

(57) ABSTRACT

An apparatus and method for adult oriented massage is presented. The apparatus includes a housing unit. An upper stimulation source is disposed within the housing unit. The upper stimulation source is operable for transferring a first percussive stimulation to a woman's lower abdomen proximate a top of a pubic bone. A lower stimulation source is disposed below the upper stimulation and is operable for transferring a second percussive stimulation to a region proximate a bottom of the pubic bone. A drive unit is disposed below the lower stimulation source for driving the upper and lower stimulation sources. A support unit supports the housing unit. At least one flexible unit enables an angle between the housing unit and the support unit to be adjusted, where the first percussive stimulation and the second percussive stimulation combine to enable the woman to achieve a beneficial stimulation.

20 Claims, 18 Drawing Sheets

METHOD AND DEVICE FOR FEMALE THERAPEUTIC MASSAGE

CROSS-REFERENCE TO RELATED APPLICATIONS

The present Utility patent application claims priority benefit of the U.S. provisional application for patent Ser. No. 61/295,683 entitled "Adult Oriented, Massage, Entertainment, and Safe Sex Educational Device", filed on Feb. 1, 2010, under 35 U.S.C. 119(e). The contents of this related provisional application are incorporated herein by reference for all purposes to the extent that such subject matter is not inconsistent herewith or limiting hereof.

FEDERALLY SPONSORED RESEARCH OR DEVELOPMENT

Not applicable.

REFERENCE TO SEQUENCE LISTING, A TABLE, OR A COMPUTER LISTING APPENDIX

Not applicable.

COPYRIGHT NOTICE

A portion of the disclosure of this patent document contains material that is subject to copyright protection. The copyright owner has no objection to the facsimile reproduction by anyone of the patent document or patent disclosure as it appears in the Patent and Trademark Office, patent file or records, but otherwise reserves all copyright rights whatsoever.

FIELD OF THE INVENTION

One or more embodiments of the invention generally relate to an adult oriented massage method and device. More particularly, the invention relates to sensual stimulation and orgasm for women.

BACKGROUND OF THE INVENTION

According to numerous studies, women typically require significantly more sexual stimulation, as well as a variety of additional factors, to achieve sensual arousal, and orgasm than men. Numerous surveys indicate that women need, on average, twenty minutes or more of intimate stimulation to achieve orgasm. Men typically require much less time. This disparity in timing is a potential source of conflict in couples, as well as unhappiness for women.

Further, surveys indicate that ten percent (10%) or more women have never been able to achieve orgasm, either alone, or with a partner. This includes both healthy women, and those with medical conditions, such as Female Sexual Arousal Disorder (FSAD).

Some studies have indicated that ninety percent (90%) of female difficulty achieving orgasm appears to be psychological in nature. This is appears to be due to anxiety about a variety of issues, including, but not limited to, concern about body image and appearance, lack of emotional connection with her partner, anxiety about pleasing her partner, as well as the possibility of pregnancy or sexually transmitted disease.

To provide appropriate stimulation, a woman's partner typically needs to focus specifically on the task of sexual stimulation. This reduces their partner's ability to fully pay attention to other aspects of emotional intimacy during stimulation. As well, women themselves typically have to focus specific attention to self stimulation. This focus on the process prevents either the woman's partner or herself from being able to fully focusing on the experience.

The requirement that women be unclothed for typical sexual stimulation introduces the risk of body fluid transfer, particularly when there is direct genital contact. For women with body image issues, the requirement of nudity is an additional stress factor that may contribute to the above referenced psychological factors causing difficulty experiencing orgasm. Further, the requirement to be unclothed limits the locations and scenarios where sexual intimacy can occur.

Numerous hand held female stimulation and massage related devices exist. However, these devices require either the woman or her partner to both hold them, and focus attention on proper use. These have the deficiency of typically requiring direct unclothed genital contact with the device. Further, their operation prevents either the woman or her partner from fully focusing on other aspects of intimacy and the experience.

Devices exist for manually holding and positioning female stimulation devices in place. These devices hold female stimulation devices in limited positions and must be manually adjusted to ensure they remain in the appropriate position. Further they do not readily allow the couple to stand or lay very close together, and limit them to certain positions. As well they require women to have unclothed genital contact, including penetration to achieve sensual stimulation and or orgasm.

Various other solutions exist that integrate female stimulation devices with mounting solutions. While these solutions and similar others allow penetrative female stimulation, they typically require that the woman sit on or straddle the device. Having to sit on or straddle the device significantly limits the possible ways a woman can be positioned. Particularly they cannot stand upright, or lay in a direct supine position. Further these solutions require women to have unclothed genital contact, including penetration to achieve sensual stimulation and or orgasm.

Other devices exist which support a reciprocating phallus that could be used in a limited number of standing positions. However the mechanical arm extending out to support the stimulation devices limit a woman's partner from standing directly in front of or very close to her. Further, this requires women to have unclothed genital contact, including penetration to achieve sensual stimulation and or orgasm.

Another device provides a pedestal support for a female penetrative stimulation device that would allow both standing and a supine position. However, due to the size requirements of the internal reciprocating hardware of this device, it's upper housing containing this hardware would have to be so large that a woman could not stand very close directly facing her partner. Further this device requires women to have unclothed genital contact, including penetration to achieve sensual stimulation and or orgasm.

Numerous massage devices exist for health and therapeutic uses. Although not expressly designed or marketed for female stimulation, they are often used for female erotic stimulation. There are numerous references on the Internet and other media related to using vibrational and related back massagers for erotic stimulation. However the context of the conversations relate to their use in lieu of traditional phallus type and vibrating female stimulation devices. These devices typically have the same limitations as the aforementioned hand held female stimulation devices. They must be held in place by the woman or her partner. They require the woman, or her partner to focus attention on the use of the device, thus distracting focus from the woman. Most massage devices must also be used unclothed for adequate stimulation.

FIG. 4 is a cross sectional view of the base portion of a prior art massager. This massager claims to be capable of smoothing the skin and fat irregularities associated with any liposuction procedure.

FIG. 5 is a cross sectional view of the base portion of a prior art massager. This percussive massager provides body massage for treating muscle tension and fatigue.

Hand held percussive massage systems can be used to provide female stimulation when manually held in place over clothing. However the optimal positioning of the device is critical and has not been referenced in prior art. Typically the approach is to use one of the percussive heads of the massager to provide stimulation at an angle upwards towards the clitoris. This is typically a very intense stimulation and can easily cause irritation. Further, the shape and arrangement of current devices prevent them from being used to most effectively cause female stimulation. A wide range of percussive massagers exists. These devices have percussive heads that can be used in a variety of ways. Most literature states the devices are primarily intended for back massage.

These above mentioned type massagers are designed so the percussive heads are connected perpendicularly to the handle. If a woman holds the percussive massager as indicated by its design, the percussive heads will be positioned perpendicular to the body axis, as these devices are customarily used for back massage, etc. The intended outcome of this would be to have one percussive head provide stimulation to the woman's clitoral region. The challenge is that in this position the other percussive head will hit the outer thigh area, and or hip joint of the woman, causing pain and potential harm.

An alternate way of holding the above percussive massager would be to hold its handle in a manner sufficiently perpendicular to the woman's body axis that the other percussive massager won't hit her upper thigh/hip. This would allow the one of the percussive heads to be in contact with the woman's groin area without the other percussive head causing injury. However, to facilitate this, the woman would have to extend her hand and arm sideways to hold the percussive heads so they are parallel to the axis of her body. This positioning would be both uncomfortable to hold and difficult to keep in proper position. Both previous methods of holding percussive massagers have the disadvantage that either the woman or her partner must focus their attention to hold it correctly. This also limits the positions she and or her partner can be in, as well as keeping them from being able to use both hands for other ways of expressing affection.

Another device has a smaller curved handle that could facilitate holding the device in a manner consistent with an individual woman using the methods proposed herein. However, it has three percussive heads. This placement of the three percussive heads provides no location to place the third head on the woman's body without it hitting the outer thigh area and or hip joint as described above.

Yet another massager has percussive massage heads that are parallel to the handle, which allow the woman to position the lower percussive head that is closer to the handle adjacent and angled upwards towards her vagina, with the lower percussive head close to her anal region and tail bone. This is significantly less difficult for holding in position over the woman's vagina. However the positioning of the percussive head distal to the handle can cause irritation to the woman's anal region and tail bone. Significantly further, this device cannot be held in a manner consistent with the methods proposed herein due to degree of the angle of the handle from its the percussive head. The handle is curved inward and would have to penetrate the woman's abdomen in order to position the percussive heads in a manner consistent with the methods proposed herein. Furthermore, even if the handle was straight, or angled outward, it would take the woman holding the device with both hands to keep it in position, thus distracting her from fully experiencing things.

Still another device is a portable percussive massager with no handle and is powered by 2 "AA" batteries. While this device, based on its shape, could be positioned properly for the method proposed herein, it has two significant challenges. First, since it is battery powered, it does not have sufficient power to generate adequate stimulating force. Secondly, if it had been designed with a larger motor and AC power, not having a handle would make it difficult to hold in place due to degree of percussive force generated. This continual movement away from the appropriate locations for stimulation would have two challenges. It would require the woman to pay focused attention on keeping it in place, thus distracting her from the experience. Further the intermittent stimulation, interrupted by it moving out of place would not be nearly as effective as the continual stimulation of the method proposed herein.

Other devices exist for both providing massage and holding massage systems in position for a variety of health and therapeutic uses. However due to their designs they have several limitations for optimal female stimulation.

One of these devices provides a vertical mounting system and attachment for a percussive massager. However, it specifically holds the percussive massager in a position where the percussive heads are perpendicular to the vertical axis of the body. This arrangement is optimal for its purpose of allowing someone to mount it to a wall and then stand or sit with their back against it. However, having two percussive heads perpendicular to the woman's torso it makes it unusable for woman to use for stimulation as referenced above.

A key issue with all the above mentioned percussive massage devices is that they are typically not designed to be used for more than 15 to 25 minutes of continuous operation. They would not be suitable for scenarios where they would have continuous operation without risk of overheating, mechanical failure, and possibly fire.

Yet another device when providing a deep massage may provide intermittent simulation over the uterine and vaginal areas via stimulation from the surface of the abdomen. However the stimulation provided by this device is not sufficient of a nature that will induce the results of the methods proposed herein.

A variety of other devices exists consisting of a table with mechanical arm(s) to hold a massage device. However, this arrangement would prevent the woman from using it while holding a partner close to her, or particularly while standing.

Further, the above mentioned hand held, and mounted percussive, and related massage devices would not provide the woman stimulation while standing, dancing and or having close frontal contact with a partner. They also easily drift out of location due to the force of the percussive action generated.

There are numerous devices are designed to be worn under women's clothing and provide sexual stimulation. These devices typically are placed over the woman's clitoris, or placed with her vagina. Examples of these are the "Venus Butterfly, strap on clitoral stimulator" and the "Vibrating Egg" vaginal insert. However, these devices still require direct genital contact. Further, they could not be shared in public without risk of transfer of body fluids.

Other devices that provide suction on the clitoris and surrounding tissue have been implemented for treating Female Sexual Arousal Disorder (FSAD). FSAD is one of the conditions that has been associated with the previously mentioned difficulty in more than 10% of the female population to experience orgasm. These devices have been shown in studies to increase blood flow and engorgement to the glans of the clitoris and increased vaginal lubrication in women with FSAD, however their effectiveness appears to be less prevalent in women without FSAD. These devices appear to work by providing suction to the glans of the clitoris and directly surrounding tissue. This negative pressure causes blood to flow into the region and produces engorgement of the glans. This increased blood flow is associated with reduction of the above FSAD. However, these devices must be placed directly on the clitoris, and depending on the device, cannot be worn under clothing or in public. Further, these devices do not directly address blood flow in the surrounding regions of the vagina, uterus and related organs. Further, these devices could not be shared between women without the risk of transfer of body fluids.

In view of the forgoing discussion, there is a need and a desire for a method and device to allow women to reliably and consistently receive intense sexual stimulation and orgasm. Furthermore, it would be desirable for a woman to be able to receive intense sexual stimulation and orgasm from a method and device where the stimulation was sustained and held in position by the device. This would allow her to focus on the experience itself, without having the distraction of holding the device in the correct position.

Furthermore, it would be desirable for a woman to be with a partner and simultaneously receive intense sexual stimulation and orgasm from a method and device where the stimulation was sustained and held in position by the device. This would allow the woman to focus on other aspects of intimacy and emotional exchange with her partner. This further would give her partner the opportunity to focus on other aspects of intimacy and emotional exchange with the woman, without having the distraction of holding the device in the correct position.

Further, it would be desirable for women to be able experience this while fully clothed. This would be desirable due to several reasons, such as the convenience of not having to remove clothing. Further, being able to remain clothed allows the woman to avoid anxiety related to body image and appearance issues that having to be unclothed might cause. Further, remaining clothed potentially reduces risk for sexually transmitted diseases, and pregnancy as well as the associated anxiety. Furthermore, being able to remaining clothed introduces a variety of new possibilities for women to explore sensuality. This includes receiving intense sexual stimulation and orgasm while being in public, dancing alone, or dancing with a partner. Remaining clothed also allows a woman to potentially experience sexual arousal and orgasm with a partner she has just met, or otherwise would not be comfortable being unclothed with, due to the above mentioned anxieties and risks.

Even further, if a woman could have intense sexual stimulation through her clothing, for some women it would be desirable to have access to "novelty rides" that appear like a motorcycle, pony, or related "circus like rides"—while the device within the "novelty ride" provided intense sexual stimulation through their clothing.

Furthermore, it would be desirable for a method and device to help women that have never experienced orgasms achieve this quickly and often unexpectedly.

Further, it would be desirable to have a method and device that could cause stimulation and related increase in blood flow in the glands of the clitoris as used in therapies for FSAD without having unclothed genital contact with a suction device.

Further, it would be desirable to have a method and device that could cause simulation, increased blood flow, and general tissue conditioning for the entire external vaginal region, as well as providing stimulation to regions of the woman's bladder, internal vaginal structure and uterus.

Further, it would be desirable to have a method and device that could cause sensual stimulation and orgasm for women in a controlled and consistent manner for performing clinical research on female sexual response.

Furthermore, being able to achieve the above while women are clothed will likely increase the probability of a more diverse group of women being willing to participate. Having a more diverse group of women willing to participate in the aforementioned research studies will likely improve accuracy.

Further, it would be desirable to have a method and device that could cause sensual stimulation and orgasm in women that could be reused in a health club type setting. This would be similar to current services such as tanning room access, automated massage services, or equivalent. This would allow women to receive the health benefits of orgasm as part of their exercise and fitness routine.

Further, it would be desirable for a method and device to allow women to expand the variety of ways they experience sensual stimulation and orgasm. This can include having the experience in public, while dancing, while being with a partner in public, as well as from different positions they have not experienced before.

Further, it would be desirable to have a method and device that would if they wished, to allow two or more women experience intense sexual stimulation and orgasm while embracing or dancing together.

Furthermore, if a method and device is used in public that provides intense sensual stimulation and orgasm for women, it would be desirable for an optional rubber or otherwise protective cover to be available on a shared device. It could be used to prevent any possible transfer of sweat or other fluids between each successive user. If this is required to be manually added and removed every time the device is used, it could be an effective tool for reinforcing the concepts of condom use and "safe sex" policies for the public. If this protective cover was required to be properly placed for the invention to operate, it would require women to address the above issues to use the device. In this educational situation the desire would be to very graphically and publicly address the following concept. If a woman would want and demand that a new protective cover is placed on the device after a woman had previously used it, shouldn't she require the same of a partner in a non monogamous relationship? The outcome desired would be for this to cause ongoing discussion about the topic, and higher adoption of "safe sex" practices.

Furthermore, it would be desirable to have a device that could be operated continuously for public or shared use. This would include having adequate ventilation and heat dissipation for the device, as well as manufacturing it out of materials capable of heavy duty application. This continual or shared public use could be both for entertainment as well as public health educational purposes.

It is therefore an objective of the present invention to provide a device and a method that satisfies the aforementioned needs and desires.

BRIEF DESCRIPTION OF THE DRAWINGS

The present invention is illustrated by way of example, and not by way of limitation, in the figures of the accompanying drawings and in which like reference numerals refer to similar elements and in which.

Figure 1:
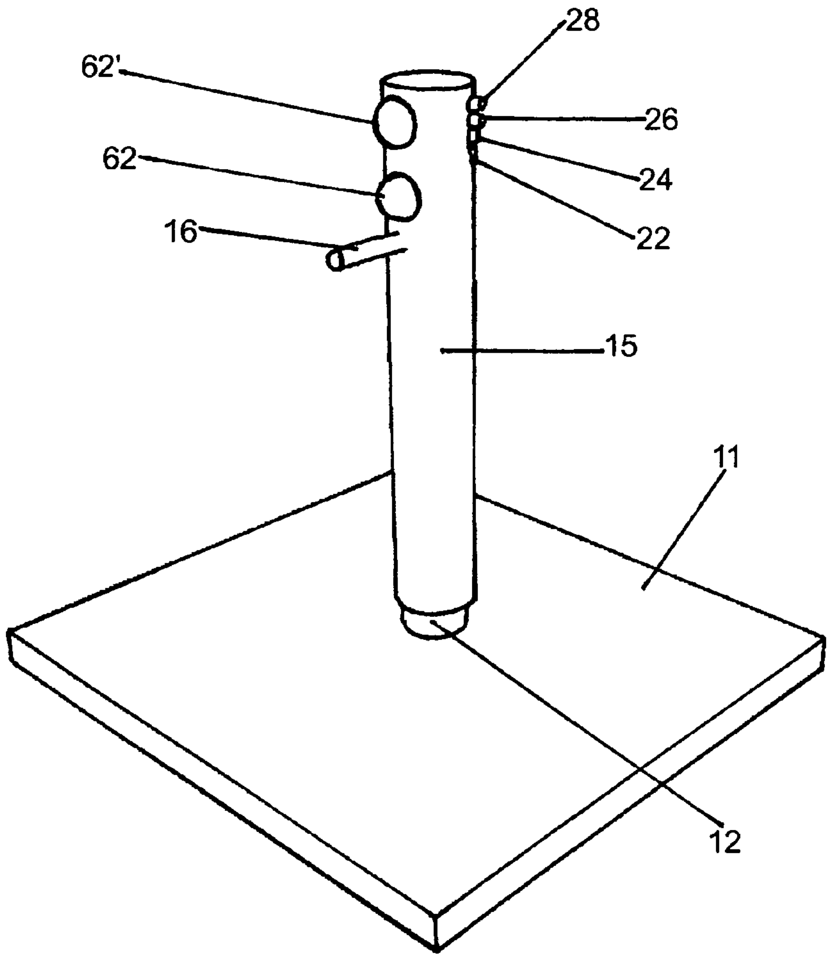
FIG. 1 is a perspective view of a housing and support structure of a basic implementation in accordance with an embodiment of the present invention.

Unless otherwise indicated illustrations in the figures are not necessarily drawn to scale.

SUMMARY OF THE INVENTION

To achieve the forgoing and other objects and in accordance with the purpose of the invention, an apparatus and method for adult oriented massage is presented.

In one embodiment an apparatus includes a housing unit, first means disposed within the housing unit for transferring a first percussive stimulation to a woman's lower abdomen, second means disposed within the housing unit for transferring, simultaneously with the first percussive stimulation, a second percussive stimulation to the woman's mons pubis region, means disposed below the second means for driving the first means and the second means, means for supporting the housing unit, and means for adjusting an angle between the housing unit and the supporting means, where the first percussive stimulation and the second percussive stimulation combine to enable the woman to achieve a beneficial stimulation. Another embodiment further includes means for assisting in positioning the first means and the second means. Yet another embodiment further includes means for at least controlling the driving means where an intensity of the first percussive stimulation and the second percussive stimulation is variable. Still another embodiment further includes means for supporting the apparatus on a floor. Another embodiment further includes means for adjusting a height of the housing unit above the floor.

In another embodiment an apparatus includes a housing unit. An upper stimulation source is disposed within an upper portion of the housing unit. The upper stimulation source being operable for transferring a first percussive stimulation to a woman's lower abdomen proximate a top of a pubic bone. A lower stimulation source is disposed below the upper stimulation source. The upper stimulation source being operable for transferring, simultaneously with the first percussive stimulation, a second percussive stimulation to the woman's mons pubis region proximate a bottom of the pubic bone. A drive unit is disposed below the lower stimulation source for driving the upper stimulation source to generate the first percussive stimulation and the lower stimulation source to generate the second percussive stimulation. A support unit supports the housing unit. At least one flexible unit enables an angle between the housing unit and the support unit to be adjusted, where the first percussive stimulation and the second percussive stimulation combine to enable the woman to achieve a beneficial stimulation. Another embodiment further includes a flexible guide disposed below the lower stimulation source and protrudes perpendicularly outward from the housing unit. The flexible guide being operable for assisting in positioning the upper stimulation source and the lower stimulation source. In yet another embodiment the flexible guide is further being operable for transferring a vibration to the woman's crotch area. Still another embodiment further includes a control unit being operable for at least controlling the drive unit where an intensity of the first percussive stimulation and the second percussive stimulation is variable. In another embodiment the control unit is further being operable for varying an intensity of the vibration. Yet another embodiment further includes a base unit for supporting the apparatus on a floor where the flexible unit joins the base unit and the support unit. Still another embodiment further includes means for adjusting a height of the housing unit above the floor. In another embodiment the control unit is further being operable for adjusting the height. Still another embodiment further includes a second flexible unit for enabling an angle between the housing unit and the support unit to be adjusted. Yet another embodiment further includes a seat. In still another embodiment the base unit comprises a facade. In another embodiment the drive unit comprises an electric motor.

In another embodiment a method includes positioning a housing unit proximate a lower abdomen of a woman where the housing unit comprises an upper stimulation source for generating a first percussive stimulation and a lower stimulation source for generating a second percussive stimulation. The method includes adjusting a height of a supporting unit for the housing unit where the adjusting positions the upper stimulation source to transfer the first percussive stimulation to a location proximate a top of a pubic bone of the woman, and the lower stimulation source to transfer the second percussive stimulation to a location proximate a bottom of the pubic bone. The method includes activating the upper stimulation source to generate the first percussive stimulation and the lower stimulation source to generate the second percussive stimulation. The method includes adjusting an angle between the housing unit and the support unit, where the first percussive stimulation and the second percussive stimulation combine to enable the woman to achieve a beneficial stimulation. Another embodiment further includes using a flexible guide protruding from the housing unit to assist in adjusting the height and or position. Yet another embodiment further includes activating the flexible guide to generate a vibration. Still another embodiment further includes adjusting an intensity of the first percussive stimulation and the second percussive stimulation. Another embodiment further includes adjusting an intensity of the vibration.

Other features, advantages, and objects of the present invention will become more apparent and be more readily understood from the following detailed description, which should be read in conjunction with the accompanying drawings.

DETAILED DESCRIPTION OF THE PREFERRED EMBODIMENTS

The present invention is best understood by reference to the detailed figures and description set forth herein.

Embodiments of the invention are discussed below with reference to the Figures. However, those skilled in the art will readily appreciate that the detailed description given herein with respect to these figures is for explanatory purposes as the invention extends beyond these limited embodiments. For example, it should be appreciated that those skilled in the art will, in light of the teachings of the present invention, recognize a multiplicity of alternate and suitable approaches, depending upon the needs of the particular application, to implement the functionality of any given detail described herein, beyond the particular implementation choices in the following embodiments described and shown. That is, there are numerous modifications and variations of the invention that are too numerous to be listed but that all fit within the scope of the invention. Also, singular words should be read as plural and vice versa and masculine as feminine and vice versa, where appropriate, and alternative embodiments do not necessarily imply that the two are mutually exclusive.

It is to be further understood that the present invention is not limited to the particular methodology, compounds, materials, manufacturing techniques, uses, and applications, described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to "an element" is a reference to one or more elements and includes equivalents thereof known to those skilled in the art. Similarly, for another example, a reference to "a step" or "a means" is a reference to one or more steps or means and may include sub-steps and subservient means. All conjunctions used are to be understood in the most inclusive sense possible. Thus, the word "or" should be understood as having the definition of a logical "or" rather than that of a logical "exclusive or" unless the context clearly necessitates otherwise. Structures described herein are to be understood also to refer to functional equivalents of such structures. Language that may be construed to express approximation should be so understood unless the context clearly dictates otherwise.

Unless defined otherwise, all technical and scientific terms used herein have the same meanings as commonly understood by one of ordinary skill in the art to which this invention belongs. Preferred methods, techniques, devices, and materials are described, although any methods, techniques, devices, or materials similar or equivalent to those described herein may be used in the practice or testing of the present invention. Structures described herein are to be understood also to refer to functional equivalents of such structures. The present invention will now be described in detail with reference to embodiments thereof as illustrated in the accompanying drawings.

From reading the present disclosure, other variations and modifications will be apparent to persons skilled in the art. Such variations and modifications may involve equivalent and other features which are already known in the art, and which may be used instead of or in addition to features already described herein.

Although Claims have been formulated in this application to particular combinations of features, it should be understood that the scope of the disclosure of the present invention also includes any novel feature or any novel combination of features disclosed herein either explicitly or implicitly or any generalization thereof, whether or not it relates to the same invention as presently claimed in any Claim and whether or not it mitigates any or all of the same technical problems as does the present invention.

Features which are described in the context of separate embodiments may also be provided in combination in a single embodiment. Conversely, various features which are, for brevity, described in the context of a single embodiment, may also be provided separately or in any suitable subcombination. The Applicants hereby give notice that new Claims may be formulated to such features and/or combinations of such features during the prosecution of the present application or of any further application derived therefrom.

As is well known to those skilled in the art many careful considerations and compromises typically must be made when designing for the optimal manufacture of a commercial implementation any system, and in particular, the embodiments of the present invention. A commercial implementation in accordance with the spirit and teachings of the present invention may configured according to the needs of the particular application, whereby any aspect(s), feature(s), function(s), result(s), component(s), approach(es), or step(s) of the teachings related to any described embodiment of the present invention may be suitably omitted, included, adapted, mixed and matched, or improved and/or optimized by those skilled in the art, using their average skills and known techniques, to achieve the desired implementation that addresses the needs of the particular application.

It is to be understood that any exact measurements/dimensions or particular construction materials indicated herein are solely provided as examples of suitable configurations and are not intended to be limiting in any way. Depending on the needs of the particular application, those skilled in the art will readily recognize, in light of the following teachings, a multiplicity of suitable alternative implementation details.

Preferred embodiments and some variations thereof provide a method and devices for facilitating female sexual stimulation and orgasm. Various embodiments of this invention may comprise of a housing that contains an upper and lower percussive massage source, as well as an optional vibrating guide. The housing may be supported by a structure that, depending on the embodiment, may be manually or electronically adjusted to the correct position. In free standing embodiments, the supporting structure may be connected to the floor, or other horizontal or vertical securing points. Further, other embodiments may be connected to supporting structures within novelty facades. In hand held embodiments the supporting structure may consist of a handle with a connection to the housing that may have its angle adjusted. Embodiments that are pneumatically powered may also be used in pools and hot tubs. Various embodiments include methods for using the above devices.

In accordance with one or more embodiments, the present invention includes methods for application of devices that provide means for a percussive stimulation source that may be directed on a woman's lower abdomen, just above the pubic bone. Means for a percussive stimulation source may be directed on the woman's mons pubis region. Means for an optional guide may provide assistance for positioning the above mentioned percussive stimulation sources at both the correct position on the woman's body and correct angle of adjustment, as well as helping hold the embodiment in place. Means for an optional vibrational stimulation source may be contained within the previously mentioned optional guide. Means for housing may contain the previous items. Means for a supporting structure that, depending on the embodiment, may be manually or electronically positioned for allowing optimal location and angle for the previously mentioned housing, as well as keeping it in proper position. This supporting structure may comprise a plurality of configurations, depending on the requirement of the embodiment. Means for an optional remote control system may control the previously mentioned items either at the device, or at a remote location via an INTERNET connection. Means for a cooling mechanism may allow continuous operation of the embodiment without overheating. In some embodiments, means for an optional novelty facade, such as, but not limited to, a motorcycle, pony, or other facades may be included. In other embodiments, means for an optional dual version, allowing for stimulation of two women at the same time utilizing a variation of the above mentioned items may be included. In some embodiments methods may provide an option for stimulation using the above items where such stimulation will work through normal clothing. In other embodiments methods may provide an option for allowing the above items to be used in a manner such that, but not limited to, a woman can stand, dance, or be positioned in a variety of other positions while receiving stimulation from the above items. In other embodiments methods may provide an option for allowing the above items to be used in a manner such that, but not limited to, a woman can stand, lay close to, or straddle a partner, while receiving stimulation from the above items.

In accordance with one or more embodiments, the present invention may also includes devices that provide means for a percussive stimulation source that may be directed on the woman's lower abdomen, just above the pubic bone. Means for a percussive stimulation source may be directed on the woman's mons pubis region. Means for an optional guide that provides assistance for positioning the above mentioned percussive stimulation sources at both the correct position on the woman's body and correct angle of adjustment, as well as help hold the embodiment in place. Means for an optional vibrational stimulation source may be contained within the previously mentioned optional guide. Means for housing may contain the previous items. Means for a supporting structure that, depending on the embodiment, may be manually or electronically positioned for allowing optimal location and angle for the previously mentioned housing, as well as keeping it in proper position. This supporting structure may comprise a plurality of configurations, depending on the requirement of the embodiment. Means for an optional remote control system may control the previously mentioned items either at the device, or at a remote location via an INTERNET connection. Means for a cooling mechanism may allow continuous operation of the embodiment without overheating. In some embodiments, means for an optional novelty facade, such as, but not limited to, a motorcycle, pony, or other facades may be included. In other embodiments, means for an optional dual version, allowing for stimulation of two women at the same time utilizing a variation of the above mentioned items may be included. Embodiments of the present invention may provide an option for stimulation using the above items where such stimulation will work through normal clothing. Other embodiments of the present invention may provide an option for allowing the above items to be used in a manner such that, but not limited to, a woman can stand, dance, or be positioned in a variety of other positions while receiving stimulation from the above items. Other embodiments of the present invention may provide an option for allowing the above items to be used in a manner such that, but not limited to, a woman can stand, lay close to, or straddle a partner, while receiving stimulation from the above items.

According to methods described herein, a device, in accordance with embodiments of the present invention, may be positioned and held in place on the woman's pelvis via a supporting structure. The device may be either aligned by the woman who knows how to position it at the correct location and angle, or an optional lower vibrating guide may be employed which assists correct positioning. In the non-limiting case where no vibrating guide is used, the woman may manually position, and uses the device in the same manner as detailed below. The device and methods used below may be performed when the woman is either clothed, or unclothed.

In the event a lower vibrating guide is employed, the device may be positioned so that its housing, containing upper and lower massage sources, is moved up and forward until the lower vibrating guide presses against the base of the woman's crotch. At that point the upper massage source will be generally located just above the woman's pubic bone, on her lower abdomen. The lower massage source will be located generally just above the woman's mons pubis region. The housing and respective massage sources will be positioned approximately parallel to the axis of the woman's upper body. In this case the massage sources may provide percussive stimulation into the woman's body at an angle that is perpendicular to the massage housing. At that point the supporting structure may allow the housing to tilt slightly from the parallel to adjust the direction of stimulation from the massage sources. Once engaged, the massage sources may provide percussive stimulation to the previously mentioned locations. This percussive stimulation may be adjusted in speed and amplitude to impart shock waves that travel into the tissue below.

It is commonly known that percussive massage devices can impart stimulation into human tissue that can travel several centimeters, depending on the nature of the tissue below. Therefore if percussive massage is applied with sufficient frequency and amplitude to the following locations on a woman, and at the appropriate angle for each percussive source, it can be concluded that the related tissues and structures will be affected. To work according to the method herein, the above mentioned percussive massage sources are positioned at the correct location and angle.

Stimulation facilitated by the upper percussive massage source has been observed to affect the tissue in the lower abdomen, including, but not limited to, the uterine ligament, bladder, internal aspects of the vagina and aspects of the uterus. Further, this percussive stimulation has been observed to induce vibration of the woman's pubic symphysis (pubic bone and related tissue). Vibration of this structure is transferred via the clitoral suspensory ligament to, but not limited to, the body of the clitoris, the crura, and glans. The upper percussive node vibrating the uterine ligament has been observed to produce the "g-spot" sensation.

Simultaneously, stimulation facilitated by the lower percussive massage source has been observed to affect tissue in, and surrounding, the mons pubis region. This includes, but not limited to, the labia major and minora, urethral opening, the body of the clitoris, both legs of the crura, the glands of the clitoris, external aspects of the vagina, the perineum and anus.

Typically far more intense stimulation may be transferred through the tissue of the mons pubis region than could be directed specifically at the glans of the clitoris. However the glands and surrounding regions of the clitoris are all affected at the same time by this regional tissue stimulation. This has been observed to cause a more mild simulation at the specific site of the clitoris, but the stimulation occurs at all parts simultaneously. Further, stimulation is simultaneously occurring on all surrounding tissue.

Furthermore, stimulation from the lower percussive massage source has been observed to cause vibration of the entire body of the clitoris. This vibration may transfer to the clitoral suspensory ligament and travel upwards to its connection at the pubis symphysis. When this vibration traveling upward from the lower massage source combines with stimulation created by the upper massage source, which is traveling downward, more intense overall stimulation is typically observed.

Even further, if the option of having a lower vibrational guide is used, the woman may elect to engage its vibration during the stimulation of the aforementioned upper and lower massage sources. This vibration may cause stimulation to the lower vaginal region, perineum, anus, coccyx and corresponding base of the spine.

The above sources of stimulation, when combined simultaneously, typically cause profound stimulation of the related tissues, resulting in increased blood and lymphatic flow, as well as stimulation of the pelvic and hypogastric nerves. This simultaneous stimulation of multiple separate nerve groups, appears to result in an amplified, or enhanced perception of overall stimulation. This typically results in women quickly experiencing a profound sexual arousal and orgasm. Further, since the stimulation is not overly intense at any specific location, many women appear to be able to achieve multiple orgasms, in quick succession, with this method.

The optional vibrational guide is used to assist the woman in easily positioning the upper and lower percussive massage sources, as well as adjusting them to the correct angle for optimal tissue stimulation. Further it can be a source of vibratory stimulation as well. This vibrational guide also assists with keeping the massage sources in place. Without it the massage sources can easily shift out of correct position and alignment, thus requiring continual attention by either the women or her partner.

The supporting structure allows the embodiment to be held in correct position and angle for optimal stimulation. Therefore, once setup, the woman may focus exclusively on the experience and not have to divide her focus between the feeling and having to hold the device in place.

Thus, the methods and devices described herein enable couples an opportunity for the women to receive physical stimulation that is managed by the device, while their partner can fully focus on other aspects of intimacy and emotional bonding. By using the device as part of their intimacy, the woman may potentially achieve both emotional and sexual satisfaction more quickly and easily due to the unique nature of stimulation, in combination with the enhanced attention from her partner. Afterwards she has the option of reciprocating for her partner. This approach addresses the aforementioned disparity in time required for sexual satisfaction between men and women.

Furthermore, embodiments of the present invention may enable the woman to be stimulated while either unclothed, or fully clothed. The option of being fully clothed, introduces numerous additional advantages:

(1) it provides the woman with convenience of not having to remove her clothing;

(2) it enables the woman to avoid anxiety related to body image and appearance issues than having to be unclothed might cause;

(3) it potentially reduces anxiety of the risk for sexually transmitted diseases, and pregnancy;

(4) it effectively eliminates the risk of pregnancy and diseases transferred by direct genital contact;

(5) if the woman remains clothed, it reduces the previously mentioned anxieties for the woman, potentially helping her overcome some of the psychological barriers to achieving orgasm;

(6) it introduces a variety of new possibilities for women to explore sensuality. This includes receiving intense sexual stimulation and orgasm while, but not limited to, being in public, dancing alone, or dancing with a partner;

(7) it enables a woman to potentially experience sexual arousal and orgasm with a partner she has just met, or otherwise would not be comfortable being unclothed with, due to the above mentioned anxieties and risks;

(8) it enables the potential for "novelty rides" for public entertainment use;

(9) it may potentially provide a method and device that causes stimulation and related increase in blood flow in the glans of the clitoris as used in therapies for FSAD, without having unclothed genital contact with a suction device;

(10) it may potentially provide a method and device that causes simulation, increased blood flow, and general tissue conditioning for the entire external vaginal region, as well as providing stimulation to, but not limited to, regions of the women's bladder, internal vaginal structure and uterus;

(11) it provides a method and device that causes sensual stimulation and orgasm for women in a controlled and consistent manner for performing clinical research on female sexual response. Furthermore, being able to achieve the above while women are clothed may likely increase the probability of a more diverse group of women being willing to participate. Having a more diverse group of women willing to participate in the study may likely improve accuracy;

(12) it provides a method and device that may cause sensual stimulation and orgasm in women that may be reused in an health club type setting. This would be similar to current services such as tanning room access, automated massage services, or equivalent. This would enable women to receive the health benefits of orgasm as part of their exercise and fitness routine;

(13) it provides a method and device to enable women to expand the variety of ways they experience sensual stimulation and orgasm from different positions they have not experienced before;

(14) it provides a method and device that would if they wished, to enable two or more women to experience intense sexual stimulation and orgasm while embracing or dancing together; and

(15) it provides a method and device for public educational use that provides intense sensual stimulation and orgasm for women while associating it with concepts of safe sex education and condom use.

Furthermore, embodiments of the present invention are designed to have adequate ventilation and heat dissipation built in. They may be manufactured from materials capable of heavy duty application. This provides the advantage of being able to operate the embodiments over an extended time period, or continuously for private, public, or shared use. Previously mentioned art typically has time limits of operation to avoid overheating and failure.

Furthermore, a smaller hand held version of the embodiment may be available for home use. In this case the supporting structure may consist of a handle with a connection to the main percussive housing where the angle may be adjusted to allow the woman to easily hold it while it is the correct position.

Furthermore, as the awareness increases that women can experience intense sensual stimulation easily, if desired through their clothing, in a variety of positions as well as while dancing, this represents a new need. This awareness will likely also cause significant public discussion, and increased acceptance of women's needs, and rights, for sexual self expression. As this public awareness of acceptance increases, women's anxieties about this topic are likely to decrease, thus making it easier to women to achieve orgasm and sexual satisfaction in general.

In accordance with a method embodiment of the present invention, a method is provided below for using at least one of various embodiments of the present invention, which present method embodiment includes a step of positioning a housing unit proximate a lower abdomen of a woman where the housing unit comprises an upper stimulation source for generating a first percussive stimulation and a lower stimulation source for generating a second percussive stimulation. The present method embodiment further includes a step of adjusting a height of a supporting unit for the housing unit where the adjusting positions the upper stimulation source to transfer the first percussive stimulation to a location proximate a top of a pubic bone of the woman, and the lower stimulation source to transfer the second percussive stimulation to a location proximate a bottom of the pubic bone. The present method embodiment further includes a step of activating the upper stimulation source to generate the first percussive stimulation and the lower stimulation source to generate the second percussive stimulation. The present method embodiment further includes a step of adjusting an angle between the housing unit and the support unit, where the first percussive stimulation and the second percussive stimulation combine to enable the woman to achieve a beneficial stimulation. The present method embodiment further includes a step of using a flexible guide protruding from the housing unit to assist in adjusting the height and or position. The present method embodiment further includes a step of activating the flexible guide to generate a vibration. The present method embodiment further includes a step of adjusting an intensity of the first percussive stimulation and the second percussive stimulation. The present method embodiment further includes a step of adjusting an intensity of the vibration.

Potential Medical Therapies of the Above Method.

Since the herein defined method causes significant tissue stimulation, and increased blood flow in the above mentioned areas, variations of it have implications for medical therapies.

The above method may be effective in addressing a variety of female medical conditions, including but not limited to;

urinary incontinence;
interstitial cystitis;
increasing chances of pregnancy in traditional, artificial insemination, and in-vitro fertilization;
certain uterine, ovarian and vaginal cysts;
premenstrual syndrome;
menopause;
female sexual arousal dysfunction.

More detailed explanations of these applications are below:

A Method for Therapy to Treat Certain Types of Female Urinary Incontinence.

Female urinary incontinence can be caused by a variety of conditions. A very common cause is due to loss of strength and tone of the urethral sphincter muscles. This could be addressed in the following manner.

The upper percussive massage source (62') produces mechanical stimulation that travels to the woman's urinary bladder. This stimulation causes a squeezing effect on the bladder, causing urine present to press against the urethral sphincter muscles. This pressure comes small pulses in cycles ranging from three to ten or more cycles per second. These pulses introduce small physical challenges to the urethral sphincter hundreds of times per minute. After daily or other interval therapy, muscular hypertrophy should result, thus strengthening and conditioning the urethral sphincter and reducing incontinence.

Furthermore, the stimulation provided by the lower percussive massage source (62) causes simultaneous stimulation for the urethral sphincter muscles directly. This stimulation results in increased blood flow and general tissue conditioning.

One therapeutic approach used is as follows: the woman would wear an absorbent napkin to address urine leakage during therapy. She would begin sessions on an empty bladder, during which she attempts to consciously squeeze the sphincter muscles. Over a period of treatments, she would gradually increase her fluid intake, and not empty her bladder prior to therapy. As she is able to hold a slightly larger volume of fluid in her bladder, the physical challenge to the urethral sphincter muscles increases.

After sufficient sessions, the conditioning of the urethral sphincters should be sufficient to allow her to maintain continence. If needed, periodic treatments may be indicated for maintenance.

A Method of Therapy to Increase the Effectiveness of Current Treatments for Interstitial Cystitis.

Interstitial cystitis is believed to be caused by chronic infection in the lining of the urinary bladder. While this condition occurs in men, it is more common in women. One reason this condition appears to be difficult to treat is that antibiotics prescribed to kill the infection are not able to reach all areas in the bladder. This is believed to be due to the folded nature of the interior of the bladder. When the bladder isn't full, it has numerous deep folds and creases. Infections in those areas are believed to be not exposed to antibiotics, and can reinfect other areas as soon as the treatments stop.

One approach to increase access of antibiotic agents to these areas would be to receive the antibiotic treatment, either by mouth, or via antibiotic fluid introduced to the bladder via catheter. While the bladder was either slightly or partially full, the above method of physical stimulation would be applied. The action of the upper percussive massage source (62') would induce significant mechanical vibration to the bladder, potentially allowing antibiotic agents to have better access to the folds and areas where the latent infection may be. Repeating this therapy at regular intervals in conjunction with antibiotic treatment should increase effectiveness of treatment. Follow up therapy after treatment, where the woman has a partially full bladder should allow the urine access to the deeper folds and help remove bacterial overgrowth in those areas.

A Method of Therapy to Increase Probability of Pregnancy Via Traditional, Artificial Insemination, and In-Vitro Fertilization.

For optimal conditions related to impregnation, the lining of the uterine lining should be fully developed and have optimal blood flow. Using the above method on a regular basis should have a stimulating and conditioning affect on the uterus, via mechanical stimulation the percussive massage source (62'). The stimulation from this source also causes vibration along the uterine ligament (204) which also connects to the ovaries. This stimulation typically increases blood and lymph flow to all tissues affected. If provided on a regular basis, this stimulation may help assist those organs function better, resulting in a more likely pregnancy outcome.

It is know that with strong orgasm, the cervix of the uterus typically tilts downward for several minutes afterwards. It is believed that if semen is already present in the vagina, this tilting action facilitates migration of sperm, present in the semen, into the uterus. These sperm are believed to follow lower viscosity flows of lower PH fluid coming from the uterus. This flow is believed to provide both a safer environment to travel through, as well as means to guide them to the fallopian tube and awaiting egg. If regular treatment with the above methods was employed prior to introduction of semen, the increased blood flow to the uterus and fallopian tubes would likely assist in optimal function of the organs. Further, if semen was introduced first, and orgasm was induced via the method above, this would likely cause the aforementioned tilting of the cervical head, thus increasing ability for sperm to migrate upwards.

In cases of in-vitro fertilization, the above method would be an excellent therapy to stimulate and precondition the uterus. The desired outcome would be to increase the thickening of the uterine lining and therefore increase probability of successful implantation.

A Method for Therapy to Increase Tissue Circulation and Potentially Reduce Uterine, Ovarian and Vaginal Cysts.

The resulting increased blood and lymph flow of the above method may provide benefit to conditions where insufficient circulation and tissue drainage has resulted in cysts and related fibroids in tissue. Percussive massage has been show effective in other areas for reducing scar tissue, increasing blood flow and general tissue healing. This therapy could be applied to women with the above conditions and follow up to see if the improved stimulation helped. The outcome of the therapy would likely depend on the nature causing the cysts, and if increased circulation would help. If therapy was beneficial, it would be done on a maintenance basis.

A Method and Therapy to Reduce Premenstrual Syndrome Discomfort.

Many women appear to experience discomfort during the completion of their monthly hormonal cycles. This discomfort appears to be due to changes in levels of circulating hormones, and the resulting effect this has on related organs. Anecdotal evidence indicates that stimulation to the uterus and ovaries during these times may help reduce the severity of their symptoms. Providing the above mentioned methods would be worth studying to see if it improves women's general feeling of well being and mood during these times.

A Method and Therapy to Reduce Symptoms of Menopause and Provide Ongoing Tissue Stimulation.

Hormonal changes related to menopause have been associated to a wide variety of symptoms and conditions. Providing the above mentioned methods may be helpful in maintaining the general health of the woman's uterus, ovaries and vagina during, and after the onset of menopause. Further, the method typically results in increased vaginal fluid production, which may help address reduced fluid and moisture production associated with menopause. Since the above mentioned methods can be done fully clothed and require no penetration, issues of vagina dryness and related discomfort are avoided. Thus stimulation can occur without the need for added lubricants.

A Method and Therapy for Female Sexual Arousal Dysfunction.

Female Sexual Arousal Dysfunction, (FSAD) is believed to have a variety of causes. In cases of clitoral vascular insufficiency, this can be due to arteriosclerosis and related causes of limited blood flow. It has been observed that reduced blood flow then results in development of scar tissue in the capillary beds, further restricting blood flow. One current physical treatment is to place a suction device over the glans of the clitoris. The lower pressure of the devices chamber surrounding the clitoris causes it to become engorged with blood. This therapy is based on the belief that the resulting engorgement both increases circulation and facilitates arousal. It is believed that ongoing application of these suction therapies help tone and restore the clitoral tissue and circulation. The above mentioned method also causes significant increase in blood flow, however in a different manner. The percussive stimulation presses both blood and lymph fluid out of the tissues when the percussive massage source head pushes into the tissues. When the percussive massage head moves back, blood and lymph are drawn back into the tissue. This phenomenon has been used therapeutically with percussive massage in other areas and is well documented. This method is also known to assist in reduction of scar tissue. The advantage with this method is that it allows both blood engorgement and return, not just engorgement. This method can also be done while the woman is fully clothed.

In FSAD apparently caused by use of anti-depressants, the above method is beneficial because it causes tissue stimulation without the need for sexual arousal or activity. However, due to the nature of the simultaneous stimulation, arousal and orgasm have been frequently observed. Having stimulation and orgasm on a regular basis, without the pressure related to having to perform with a partner frees women from these anxieties. As stimulation of this nature continues on a regular basis, it will likely assist women in further developing the ability to more easily achieve sexual response elsewhere.

The above mentioned methods can also be used by women with their partners. In this case the method and device assist them with stimulation and being able to focus on other aspects of intimacy with their partner.

FIG. 1 is a perspective view of a housing and support structure of a basic implementation in accordance with an embodiment of the present invention. A supporting platform 11 or base connection houses power sources, optional additional cooling fans, control and related equipment. These internal components are not shown but are well known to one skilled in the art. A covering for the supporting structure 12, or other connecting and supporting structures, extends from the supporting platform. In this embodiment, it is tube shaped, however it can have numerous possible configurations such as, but not limited to, rectangular, oval, triangular, etc. This covering is slightly smaller in size than the upper supporting structure 15 that slides around it. In many embodiments, the covering material may be flexible so it can flex with the movement of the structure supporting it internally. In this embodiment, the upper supporting structure 15 is continuous with the housing for the massage system 62 and 62' and optional vibrating guide 16. The upper area of the housing contains the optional vibrating guide 16 which is a flexible structure protruding perpendicularly from the housing. The lower massage node 62 is above the vibrating guide. The upper massage node 62' is above the lower massage node. Both massage nodes typically are of hemispherical shape where they extend from the housing and made of a semi firm material such as, but not limited to, rubber, silicon, composite materials, etc. In other embodiments the massage nodes may have different shapes such as, but not limited to, egg shaped, etc. The massage nodes of the current embodiment are approximately 4 centimeters in diameter, and extend approx 6 centimeters out of the housing at resting position. However additional shapes, sizes, materials, and confirmations of the massage nodes are also possible. In some embodiments, alternate sets (not shown) of massage nodes 62 and 62' are provided for attachment to the present invention. These massage nodes might be made of different materials with different degrees of firmness, potentially ranging from very soft to hard. As well each respective node might have different shapes or sizes. This enables the user to select a desired shape and feel.

Controls are located near the top of the housing on the side lateral to the location of the upper and lower massage nodes, and optional vibrating guide. In this embodiment, when the massage nodes are facing forward, the controls are located on the right side of the housing. In other embodiments the controls may be on the left side of the housing. These controls may include, but not limited to, a down toggle button 22 that allows supporting structure to lower until it reaches the bottom of its range where it automatically stops, a up toggle button 24 that allows supporting structure to raise until it reaches the top of its range where it automatically stops, a vibrating guide dual On/Off switch and vibration intensity control 26, and a dual massage node On/Off switch and node stimulation intensity control 28. In other embodiments these controls may also be incorporated as part of a remote control system that is, but is not limited to, wired, wireless, or a remote network or Internet application. In some embodiments a remote application may operate on wireless devices such as, but not limited to, smart phones and tablet devices.

In this embodiment, the housing 15 is tube shaped and approximately 10 centimeters in diameter, extending up from the base. The basic tube shape of this embodiment is small enough that two people could stand or lay close to each other with the tube at the woman's pelvic area without the size of the tube significantly preventing their proximity. However, one skilled in the art would appreciate that it could have many other shapes, diameters or configurations depending on the needs and functions the embodiment address.

Figure 2:
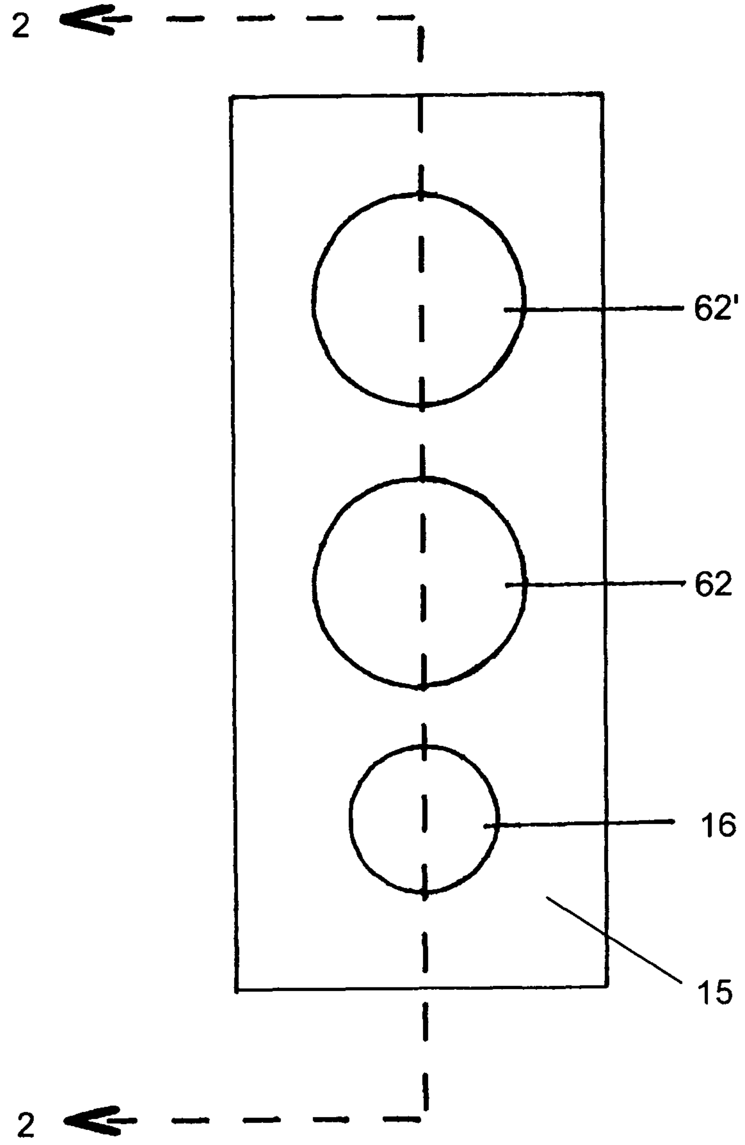
FIG. 2 is a front view of the housing of a basic implementation in accordance with an embodiment of the present invention.

FIG. 2 is a front view of the housing of a basic implementation in accordance with an embodiment of the present invention. The internal components of the upper and lower massage nodes, as well as the optional vibrating guide are contained within the upper area of the housing. Referring to FIG. 2, their external positioning on this embodiment is detailed as the housing 15, the optional vibrating guide 16, the lower massage node 62 and the upper massage node 62'.

Figure 3:
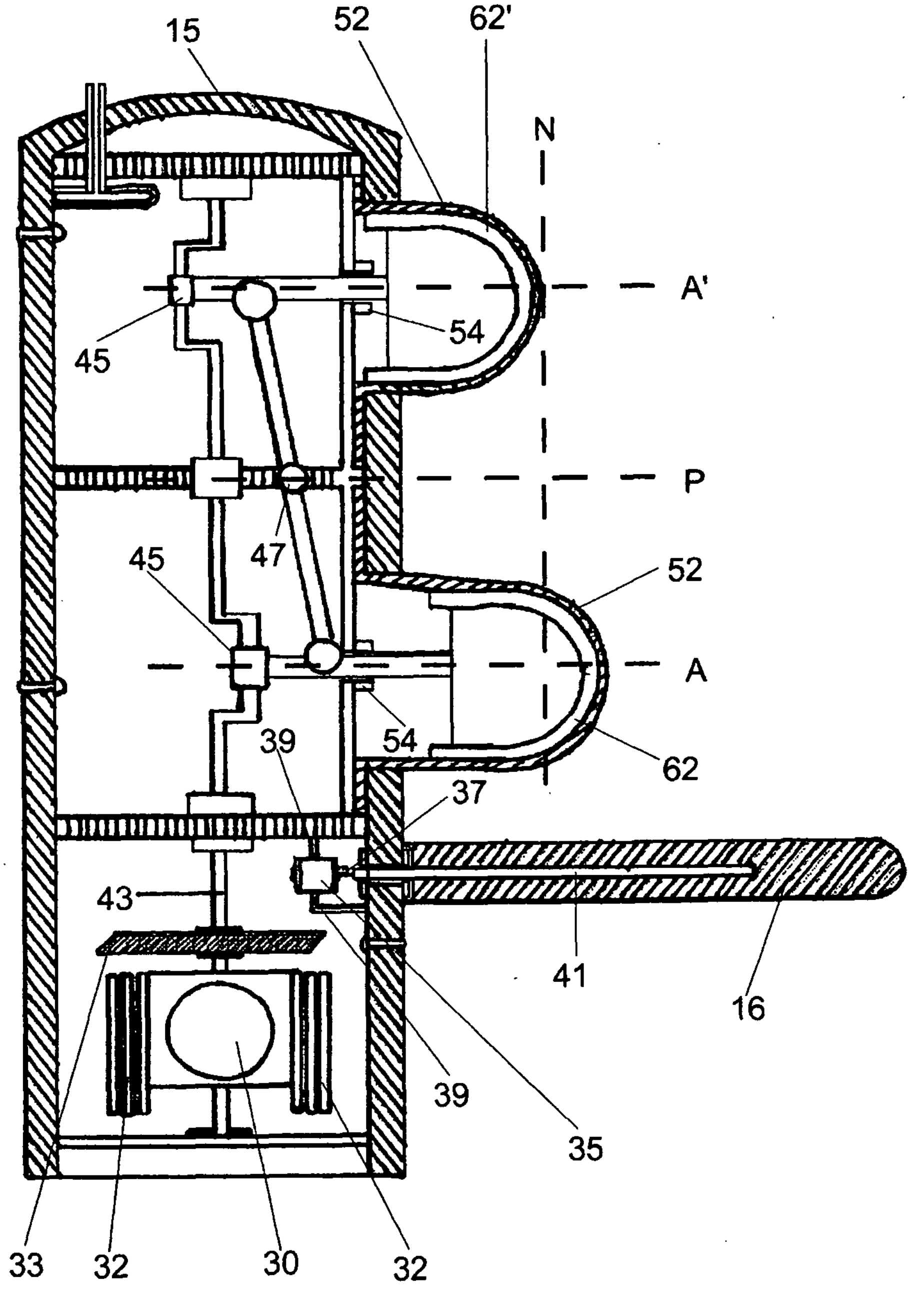
FIG. 3 is a cross sectional view taken along line 2-2 of FIG. 2 in accordance with an embodiment of the present invention.
Figure 4:
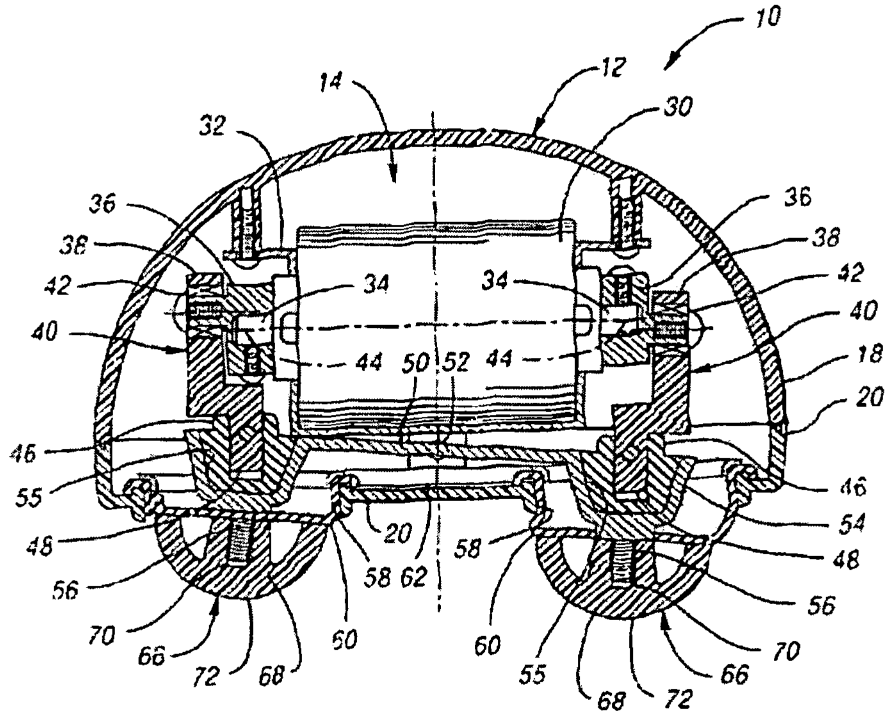
Fig. 4 Prior Art
FIG. 4 is a cross sectional view of the base portion of a prior art massager.
Figure 5:
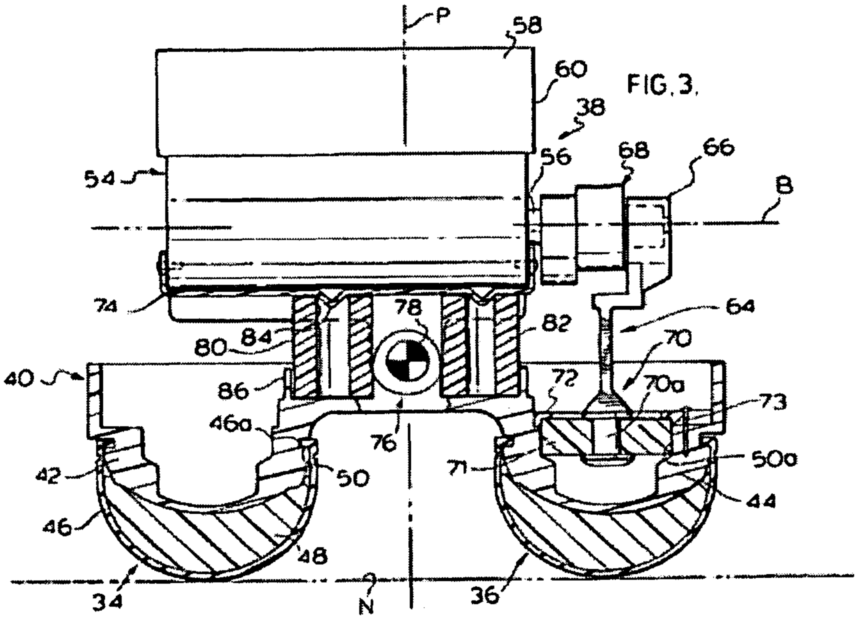
Fig. 5 Prior Art
FIG. 5 is a cross sectional view of the base portion of a prior art massager.

FIG. 3 is a cross sectional view taken along line 2-2 of FIG. 2 in accordance with an embodiment of the present invention. The housing includes a drive unit 30 contained within. Depending on the particular embodiment, this drive unit 30 is connected via a variety of means to a lower massage node 62 and upper massage node 62'. These two massage nodes provide an external massage surface that in contoured symmetrically about a median plane P generally perpendicular to the notional plane N representing a surface to be massaged. The actual massage surfaces of the massage nodes 62 and 62' are generally hemispherical, with the nodes being symmetrical around plane P. The surface of the housing 15 and underlying structure is situated in a way as to provide each massage node 62 and 62' about axes A and A' respectively which are disposed parallel to the median plane P.

In the present embodiment a single cam shaft 43 extends from the drive unit 30 to the massage nodes 62 and 62'. The drive unit 30 is located below the massage nodes 62 and 62' and is separated by a partition from the portion of housing 15 where massage nodes 62 and 62' are located. This enables minimizing the cross sectional width of housing 15 and mitigates the transfer of heat from drive unit 30 to massage nodes 62 and 62'. Additionally, the motor used has heat sink 32 attached to the body of the drive unit 30. An additional optional cooling and ventilation fan 33 is attached to the motors drive shaft. The heat sink and cooling fan are combined in a way to ensure the massage system can run continuously under normal loads at ambient temperature without overheating, or requiring intermittent shut down periods to cool off.

Although the drive unit 30 in this embodiment is a motor, other drive units contemplated include the use of pneumatic components or electromagnetic technologies similar to that of a solenoid. Each massage node 62 and 62' may be coupled to an electromagnet via coupling means know in the art. When the electromagnet is energized, the coupling means forces the massage node 62 and 62' away from the electromagnet, thereby producing movement. At the same time the one electromagnet is energized, the other electromagnet coupled to the other massage node 62 is de-energized and pulling the massage node 62' towards the electromagnet thereby producing movement. When the energizing is synchronized properly, the movement of the massage nodes can produce a percussive effect.

Although the above embodiments describe the massaging effect utilizing percussive motion, one skilled in the art would appreciate that any means may be utilized to create a massaging effect including vibratory or other types of stimulation causing motion.

Referring to FIG. 3, the vibrating guide 16 is attached to the housing 15 below the lower massage node 62. One embodiment of the vibrating guide, it is a tube shaped structure approximately 16 centimeters long and 5 centimeters wide, with a rounded tip. Typically the exterior is made of a soft rubber material that has a channel inside running from the base of the vibrating guide to approximately 10 centimeters inside. This channel contains a flexible tube 41 which attaches to and through a rubber grommet on the side of the housing. This tube opens inside the housing 15 and contains an internal shaft with an offset weight attached to the shaft 37 positioned on one side of the shaft. The internal shaft and bushings are not shown in FIG. 3 but are located within the flexible tube 41. The location of the offset weight attached to the shaft 37 varies depending on the embodiment, but can be located within the housing 15 or within the flexible tube 41. The shaft has a bushing located at the end of the tube, as well as a bushing at the end of the tube. The bushings allow the shaft to turn freely within the tube. The shaft is then attached to the drive shaft of a motor 35. The motor 35 is attached to the interior housing 15 via vibrationally damped connections 39. The power wires for the motor 35 are not shown from the angle in the drawing.

In operation, when motor 35 is engaged, it rotatably drives its shaft. This in turn causes the attached shaft 37 to rotate. As this attached shaft rotates, the unbalanced center of mass from the weight results in a shaking of the shaft relative to the speed of the motor turning. The motor 35 can be turned on or off or have its speed be controlled via an exterior control 26. This external control 26 may be attached to the housing 15 or to a remote control system connected via wire, wireless, network or Internet connection application.

Figure 6:
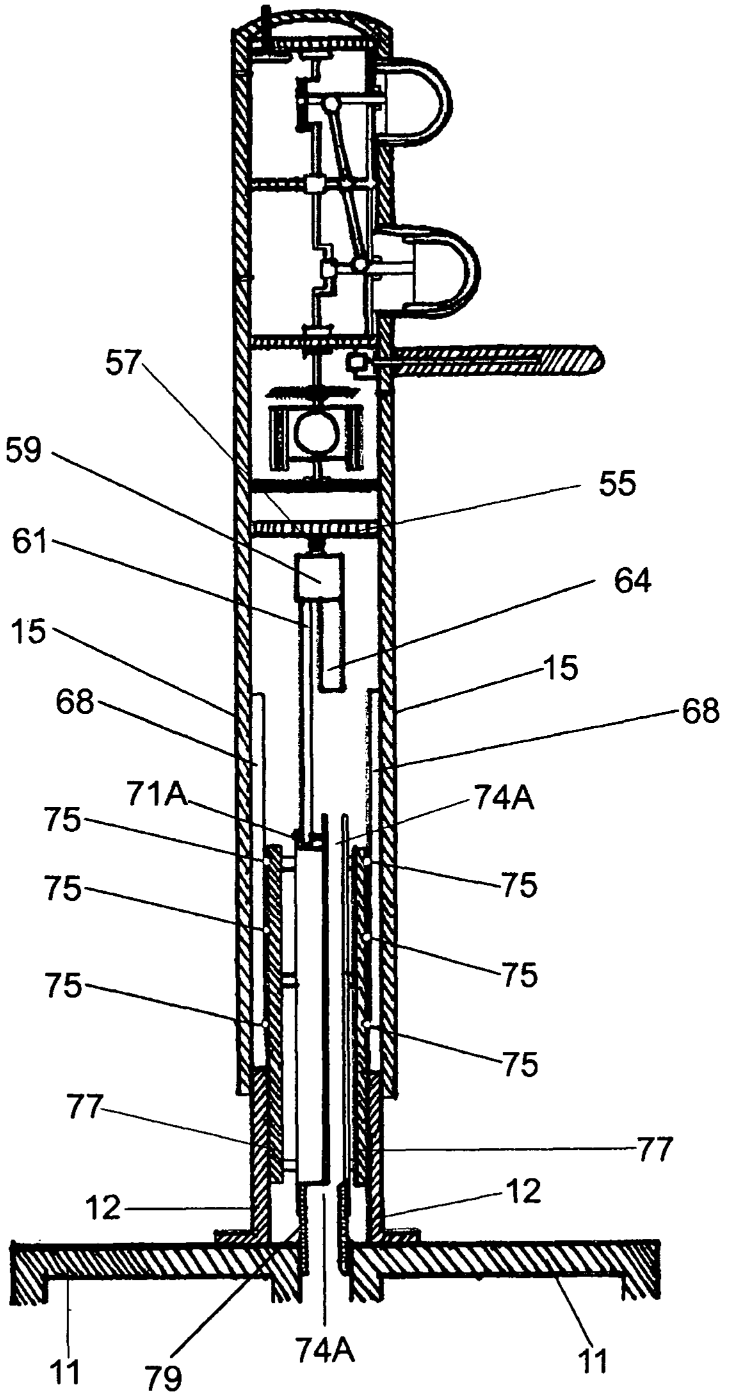
FIG. 6 is a cross sectional view of a housing and support structure of a basic implementation in accordance with an embodiment of the present invention.

FIG. 6 is a cross sectional view of a housing and support structure of a basic implementation in accordance with an embodiment of the present invention. The supporting platform 11 has a centrally located opening with a reinforced base at the opening. A flexible heavy duty spring structure 79 is attached to both the reinforced base of the supporting platform 11 below, and above to the lower internal supporting structure 71A. This spring structure is connected to both structures via bolts, welding or equivalent structurally valid connection as needed by the particular embodiment. A covering 12 for the supporting structure 71A is attached to the supporting platform 11 via screws or whatever connection is appropriate. The covering 12 encloses the inner lower internal supporting structure 71A and extends up approximately 25 centimeters from the supporting platform. The covering 12 is slightly smaller in size than the upper support structure and housing 15. In this embodiment the upper support structure and housing are continuous. The covering is inserted inside the bottom of the upper support structure and housing 15 so that the housing slides around the cover. In other embodiments this upper support structure may be separate from the housing. This covering is made of a rubber or rubber like flexible material that will bend or flex to allow the upper supporting structure and housing to move as needed. The upper portion of the lower internal supporting structure 71A attaches via screws to the interior part of sliding rail 77. This inner part of the sliding rail 77 connects via multiple self contained rollers 75 to connect to outer part of the sliding rail 68. The outer sliding rail 68 is attached to the inside of the upper support structure and housing 15 via screws. At least two, or more, of the above rail assemblies are present. A channel 74A runs from the interior of the supporting platform 11 up through the flexible heavy duty spring structure 79, and through the interior of the inner lower internal supporting structure 71A opening up to the interior of the upper support structure and housing 15. Power and control wires run from the interior of the supporting platform 11 through this channel to the massage nodes, optional vibrating guide, optional linear actuator or related height adjustment equipment, and any related equipment. In embodiments that have optional electric height adjustment and positioning, the following additional equipment may be included. A linear actuator is a device known in the art, typically consisting of control housing and gear box 59, a motor housing 64 and a retractable stroke rod 61. Power and control lines for the linear actuator are not shown in this view due to the angle. In other embodiments other equipment and ways for electrically adjusting length that are readily known to those skilled in the art may be used. In this embodiment, the base of the linear actuator 64 is attached via a vibrationally damped connection 57 to an internal structural member 55 that is part of interior of upper support structure and housing 15. The other end of the linear actuator, at the tip of its stroke rod 61 is connected via a nut and bolt, or other appropriate connection to the lower internal support structure 71A.

In operation, when DC power is applied to the linear actuator in this embodiment it causes the stroke arm 61 to extend for a range of approximately 18 centimeters. However different stroke ranges might be preferable for different embodiments. Once it has reached its maximum extension, it automatically stops. When the polarity of the DC is reversed, the stroke arm 61 retracts until it has returned to its original position. Once fully retracted it automatically stops. When an operator applies DC power of the appropriate polarity via the external controls, toggle switches 22 and 24, the linear actuator extends and pushes against the upper vibrational damped connection 57 and the lower connection to the lower internal support structure 71A. This causes the upper supporting structure and housing to rise up from its original resting position. As it raises it slides over the flexible cover 12. If this DC power is continually applied, the upper supporting structure and housing 15 will eventually reach the maximum extension length of approximately 18 centimeters. When fully extended, the flexible covering still runs inside the upper support structure and housing 15 by approximately 7 centimeters. This overlap provides continuous coverage, thus preventing an operator or other outside items being able to gain access to the interior of the device. If the upper supporting structure and housing 15 is pushed against, it will flex from the inner spring joint at the base, thus allowing it to move left, right, backwards and forwards. When an operator presses the above mentioned toggle switches 22 and 24 appropriately, the DC power will be reversed and the linear actuator will retract to its resting position, thus causing the upper supporting structure and housing 15 to lower back to its original resting position. It should be noted that with this arrangement, the upper supporting structure and housing 15 can be flexed in multiple ranges of motion around the horizontal axis while stationary, being raised or lowered.

The present invention also provides various methods for using the herein defined device embodiments. One method for using the basic embodiment referenced in FIG. 1 is for a woman either clothed or unclothed to stand adjacent to the housing 15 with her legs approximately shoulder width apart. Her feet are extending slightly past the housing 15 on each side. She, or someone else, then activates the toggle button 24 on the side of the device or a remote, or other control system to cause the housing 15 to raise up until the vibrating guide begins to press up against the base of her crotch. In embodiments which don't have electric adjustment the woman would manually raise or adjust the height of the housing. At that height, the lower massage node 62 should be approximately adjacent to the mons pubis region of her pelvis. The upper massage node 62' should be approximately adjacent to her lower abdomen, just above her pubic bone (pubis symphysis). She then will activate the massage nodes by turning on the switch 28 and intensity control. This control will be either on the side of the device or a remote, or other control system.

Once engaged, the lower massage node 62 will stimulate the tissue in the mons pubis region with the stimulation being directed along axis A referenced in FIG. 3 for the device. The upper massage node 62' will both stimulate the tissue in the lower abdomen related tissue attached to the pubis bone, with the stimulation being directed along axis A' referenced in FIG. 3 for the device. The woman will then lean or step slightly forward against the housing 15, causing it to tilt back and thus change the angle of the upper and lower massage nodes to achieve optimal stimulation of the related tissues. If desired, the woman may also activate the vibrational aspect of the vibrating guide 16 by via the vibrating guide dual On/Off switch and vibration intensity control 26. Once the vibrating guide is turned on, the woman may adjust the intensity of stimulation to the preferred level. At this point the woman is free to move her hips and perform dancing like motions if desired. As she moves, the vibrating guide will assist with keeping the lower and upper massage nodes in the correct location. As well since the diameter of the embodiment is typically 12 centimeters, she can have a partner stand close to her and embrace.

Figure 7:
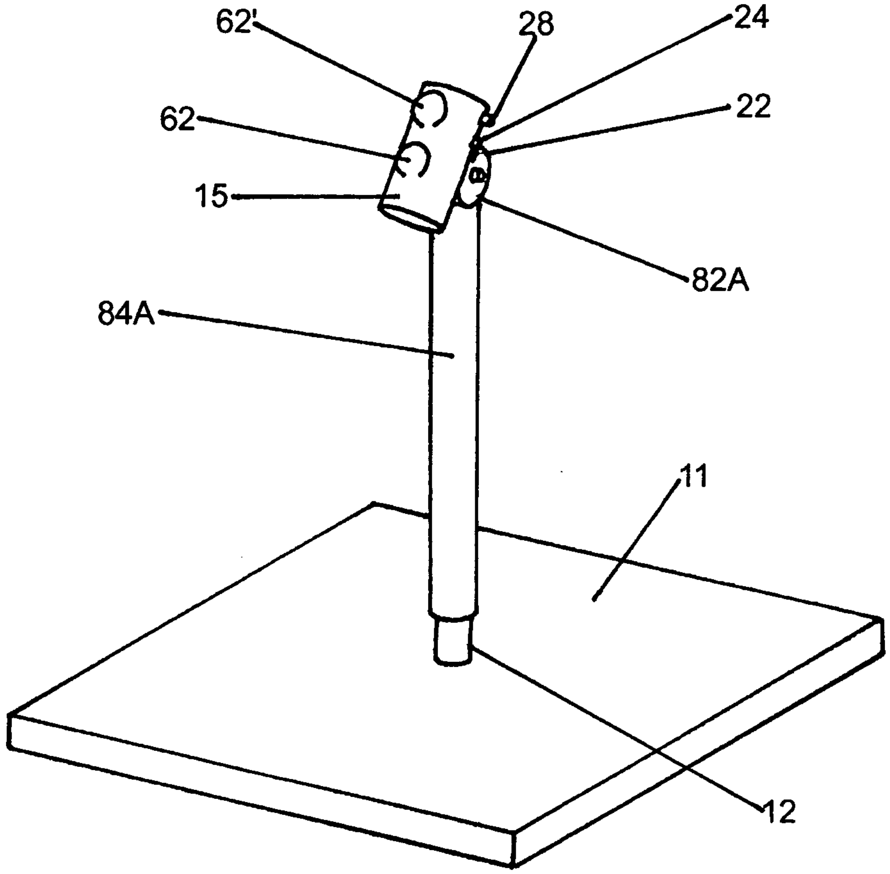
FIG. 7 is a perspective view of a basic implementation where a flexible hinged joint connects the middle rear portion of the housing to the supporting structure in accordance with an embodiment of the present invention.

FIG. 7 is a perspective view of a basic implementation where a flexible hinged joint connects the middle rear portion of the housing to the supporting structure in accordance with an embodiment of the present invention. This embodiment of the invention includes all the previously mentioned aspects of the basic embodiment, including: a Supporting platform 11; a covering for the lower internal supporting structure 12; a lower internal supporting structure 71A—not in view due to it being contained with the aforementioned cover 12; an additional upper supporting structure 84A; a flexible hinged connection 82A between the additional upper supporting structure 84A and the housing 15; a housing 15 as well comprising; an optional vibrating guide 16—not shown; a lower massage node 62; an upper massage node 62; controls with similar function to the basic embodiment, including 22, 24, 28, and 26—not shown, but would be present if the optional vibrating guide was present.

The operation of the embodiment referenced in FIG. 7 is similar to the operation of the basic embodiment referenced above, with the exception that the flexible hinged connection 82A allows the housing to have an additional range of motion. This allows the housing to tilt independently from upper supporting structure in an axis perpendicular from the upper supporting structure. In some variations of this embodiment, the supporting platform and upper supporting structure are statically attached and not flexible. As a result the only range of motion for adjustment of the housing 15 comes from the flexible hinged connection 82A.

Figure 8:
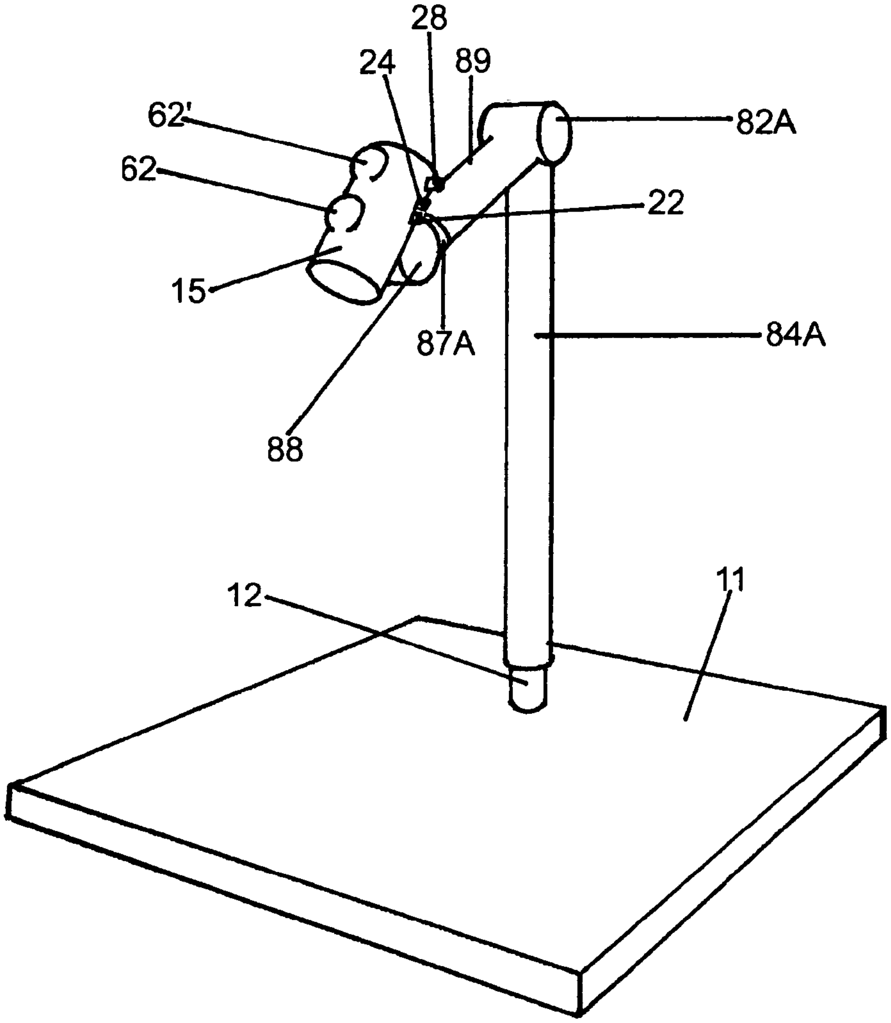
FIG. 8 is a perspective view of a basic implementation of the embodiment from FIG. 7 where the flexible hinged joint connects to a secondary optionally adjustable length support structure and that structure connects to an additional flexible hinged joint connecting it to the main supporting structure in accordance with an embodiment of the present invention.

FIG. 8 is a perspective view of a basic implementation of the embodiment from FIG. 7 where the flexible hinged joint connects to a secondary optionally adjustable length support structure and that structure connects to an additional flexible hinged joint connecting it to the main supporting structure in accordance with an embodiment of the present invention. This embodiment of the invention includes all the previously mentioned aspects of the embodiment referenced in FIG. 7, including: a Supporting platform 11; a covering for the lower internal supporting structure 12; a lower internal supporting structure 71A—not in view due to it being contained with the aforementioned cover 12; an upper supporting structure 84A; a flexible hinged connection 82A connecting the upper supporting structure 84A to; an additional supporting structure 89 with the option to adjust its length via an additional length extension mechanism 87 contained with the supporting structure of 89 comprising a mechanism similar to that described in the linear actuator description referenced in FIG. 6; a protective cover over the optional extension 87A; a hinged flexible connection 88; and a housing 15 as well comprising; an optional vibrating guide 16—not shown in this drawing; a lower massage node 62; an upper massage node 62; controls with similar function to the basic embodiment, including 22, 24, 28, note that in this drawing 26 is not shown, but would be present if the optional vibrating guide was present.

The operation of the embodiment referenced in FIG. 8 is similar to the operation of the embodiment referenced in FIG. 7, with the exception that having the additional flexible hinged connection 88 connecting housing to the additional upper support structure 90 provides even more degrees of motion and freedom. This allows the housing to tilt independently from upper supporting structure in an axis perpendicular from the upper middle support structure. Further the additional hinged joint allows the support structure to tilt independently in another axis independent from the other support structure. In some variations of this embodiment, the supporting platform and upper supporting structure are statically attached and not flexible. As a result, the range of motion for adjustment of the housing 15 comes from the flexible hinged connection 88, and the flexible hinged connection 82A.

Figure 9:
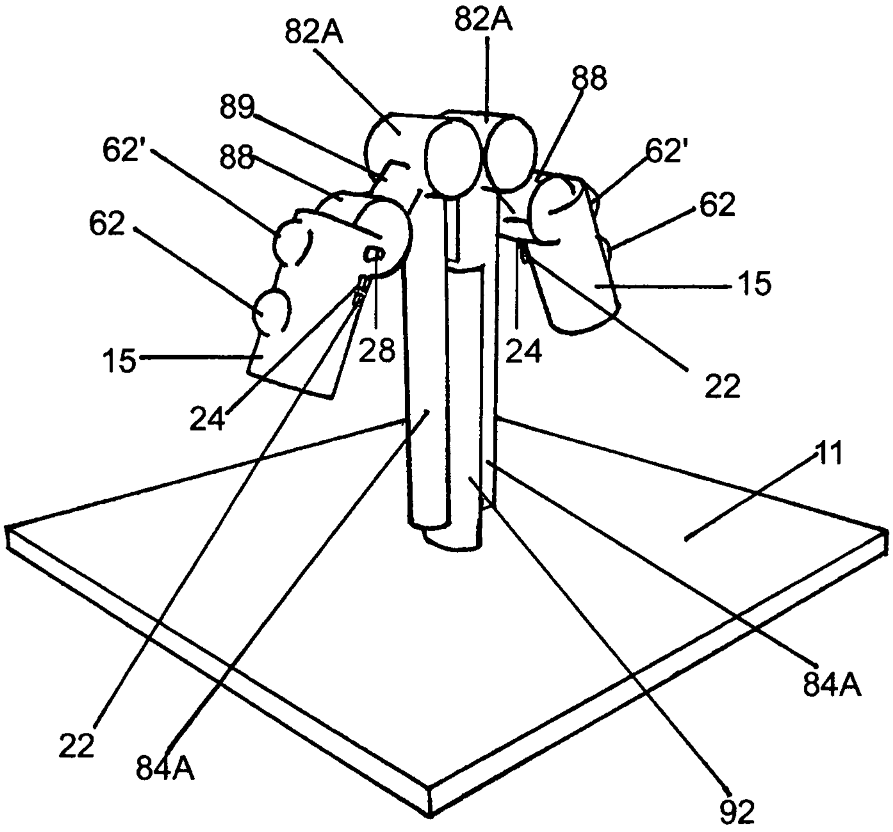
FIG. 9 is a perspective view of the embodiment from FIG. 8 modified so that it can function simultaneously for 2 users in accordance with an embodiment of the present invention.

FIG. 9 is a perspective view of the embodiment from FIG. 8 modified so that it can function simultaneously for 2 users in accordance with an embodiment of the present invention. This embodiment comprises two or more of the embodiments referenced by FIG. 8 with the modification that instead of their upper support structures 84A connecting to the supporting platform, they instead both connect to a dual supporting structure 92 that allows two or more independent structures, such as those described 84A to connect to it and travel via an internal track to allow either manual or electronic adjustment of the height.

The operation of the embodiment referenced in FIG. 9 is identical to the operation of the embodiment in FIG. 8, with the exception that it can be used simultaneously by two women.

Figure 10:
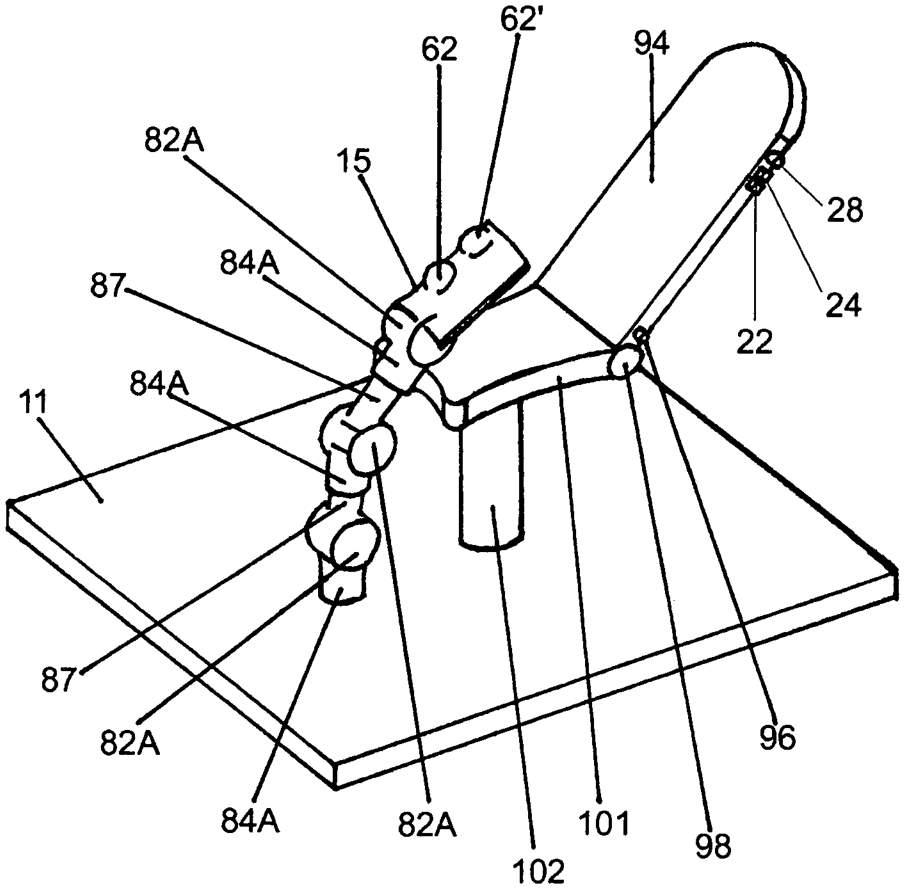
FIG. 10 is a perspective view of a basic implementation where a user's partner can sit in a chair while the user straddles both the housing and the partner in accordance with an embodiment of the present invention.

FIG. 10 is a perspective view of a basic implementation where a user's partner can sit in a chair while the user straddles both the housing and the partner in accordance with an embodiment of the present invention. The embodiment referenced in FIG. 10 is similar in arrangement to the embodiment previously referenced in FIG. 8, with the following exceptions. Additional flexible hinged joints and supporting structures are added to increase the range of positioning for the housing 15. This could also be replaced by a completely flexible tube or similar structure if desired. A chair is present that the housing can extend over. The controls for the massage nodes, and if present the optional vibrating guide, are on the back of the chair.

The operation of the embodiment referenced in FIG. 10 comprises the woman's partner sitting in the chair and then the woman positioning the housing 15 either manually or electronically so that it rests just above the lap of the woman's partner. The woman then straddles the housing 15 and adjusts its angle and position for optimal stimulation.

Figure 11:
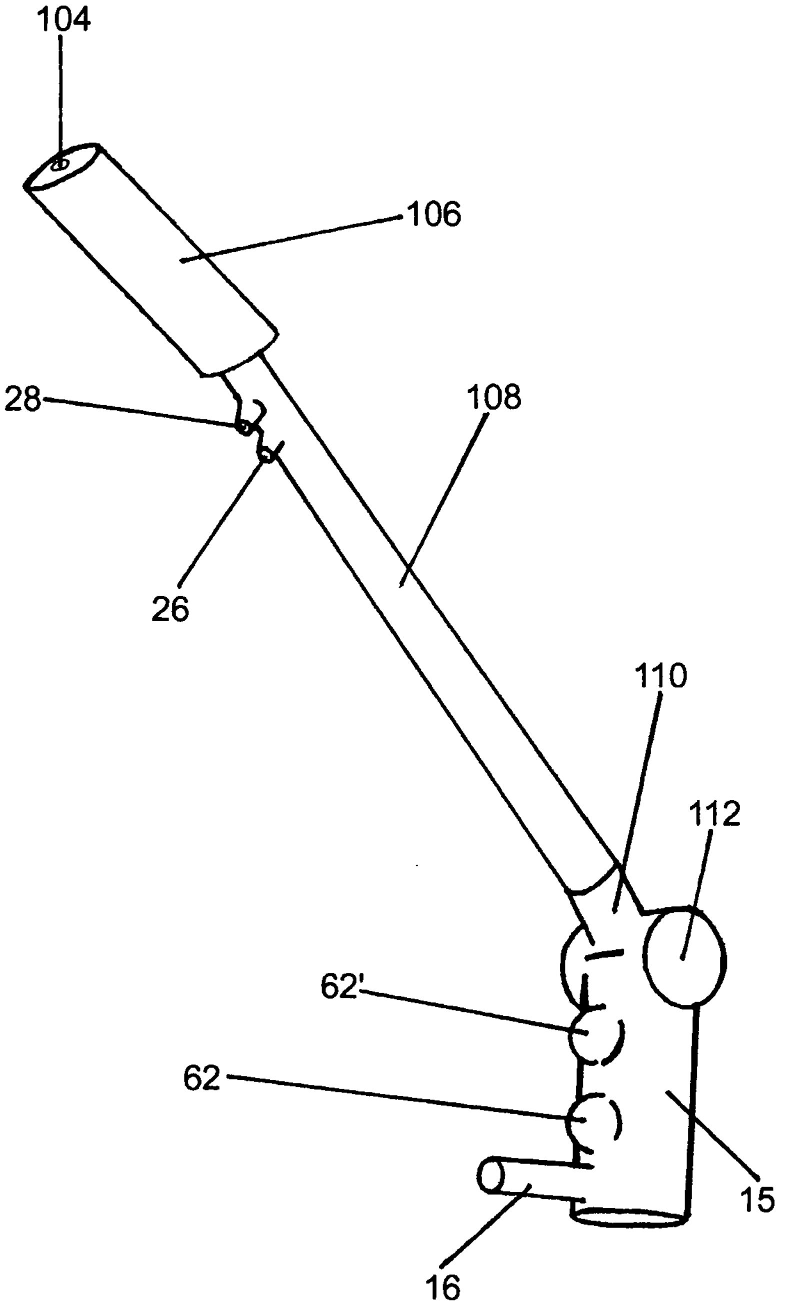
FIG. 11 is a perspective view of a basic implementation of a hand held version in accordance with an embodiment of the present invention.

FIG. 11 is a perspective view of a basic implementation of a hand held version in accordance with an embodiment of the present invention. In this embodiment the optional vibrating guide 16 is at the base of the housing 15. The lower 62 and upper 62' massage nodes are above. A manually adjustable hinged connection 112 is integrated into the top, or otherwise appropriate area of the housing. This hinged connection 112 allows the flexible "tube" to be moved at least 190 degrees around its connection and has an extension section 110 at its top. This extension top attaches to a flexible "tube" 108 or related support structure. This "tube" allows sufficient distance for the woman to easily hold it for self stimulation. Further, the hinged connection 112 allows the angle between the flexible "tube" and the housing to be adjusted manually. At the distal end of the flexible "tube" are controls for the massage nodes 28 and optional vibrating guide 26, as well as a handle 106 and a location 104 where a power cable would extend from the handle power cable not shown.

The operation of the embodiment referenced in FIG. 11 comprises multiple possible scenarios, as well as other that will become apparent with further use. In one non-limiting scenario, the woman would lie on her back and place the housing over her pelvic area, with the handle 106 pointing towards her chest and the lower vibrating guide 16 between her legs. She would then pull the handle upwards further towards her upper body until the vibrating guide was firmly positioned in her crotch area. At that point she would turn on the lower and upper massage nodes 62 and 62' and adjust the angle of the housing 15 so the axis A and A' are pointing to the appropriate previously defined area. She would then adjust the angle of the hinged connection 112 so that it was laying flat against her abdomen, or whatever position was comfortable. At that point she would, if desired, turn on the vibrational aspect of the vibrating guide via the control 26 on the flexible "tube". A variety of positions is possible using the above mentioned procedure. An alternative is to turn the adjustable hinged connection 112 so the flexible "tube" is almost completely behind the housing. Then an additional support plate could be attached to the flexible "tube" 108—note the support plate is not shown. With this configuration the woman could use the hand held version either standing in a manner similar to the operation for the embodiment from FIG. 1 or adjusting the position so she could straddle a partner in a manner similar to the operation for the embodiment from FIG. 10. Multiple arrangements and configurations of the hand held version are possible, including different length and shaped "tubes", handles, housings, hinged joints, power connection options, as well as the option for an embodiment to be battery, or pneumatically powered.

Figure 12:
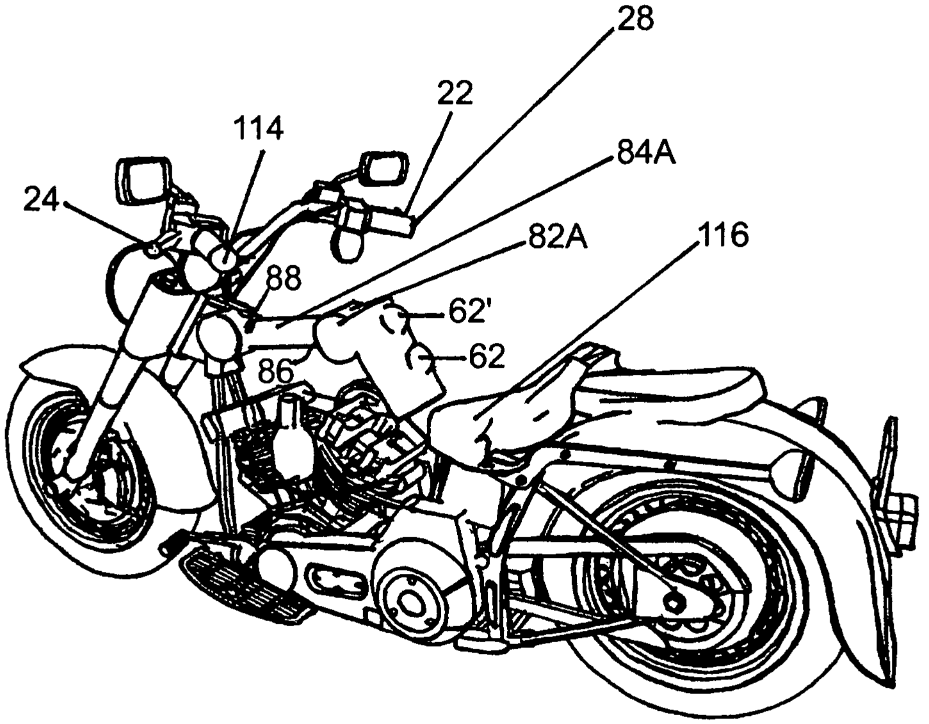
FIG. 12 is a perspective view of a basic implementation showing the housing and support structure integrated into a motorcycle facade in accordance with an embodiment of the present invention.

FIG. 12 is a perspective view of a basic implementation showing the housing and support structure integrated into a motorcycle facade in accordance with an embodiment of the present invention. The embodiment in FIG. 12 is similar to the configuration of the embodiment in FIG. 8, with the modification being that it is integrated into a novelty facade, such as a motorcycle. This only one possible embodiment, virtually any novelty facade is possible, and will be apparent to those familiar with the art.

The operation of this embodiment is for the woman to sit on a seat on the motorcycle facade and use it in a manner similar to the operation detailed for FIG. 10. In this case the woman straddled the housing 15 while sitting on the seat of the motorcycle.

Figure 13:
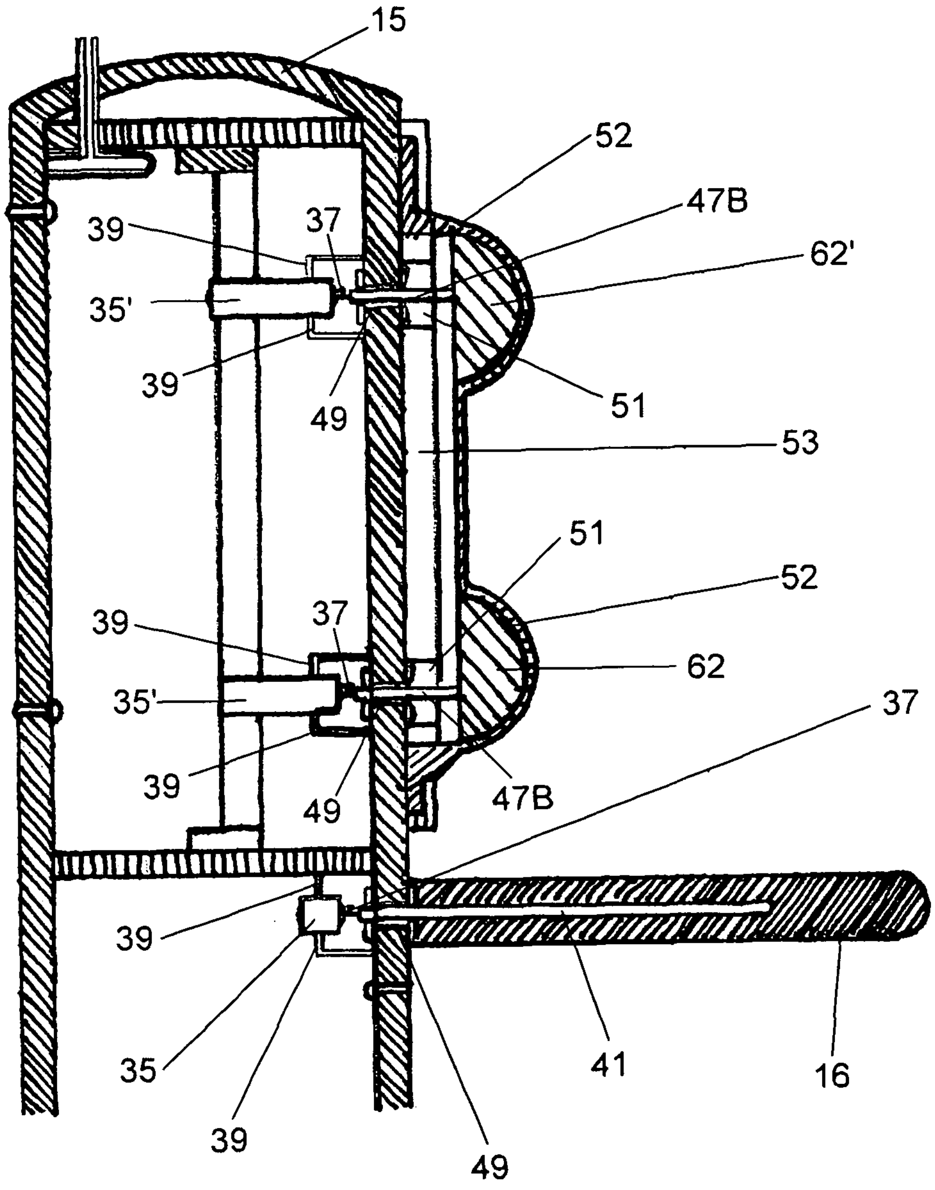
FIG. 13 is a cross sectional view of a basic implementation where a type of vibrational source is used in accordance with an embodiment of the present invention.

FIG. 13 is a cross sectional view of a basic implementation where a type of vibrational source is used in accordance with an embodiment of the present invention. The embodiment in FIG. 13 uses vibrational stimulation instead of percussive for the lower 62 and upper 62' massage nodes. Otherwise this housing 15 with included optional vibrating guide could be substituted for any embodiment.

Figure 14:
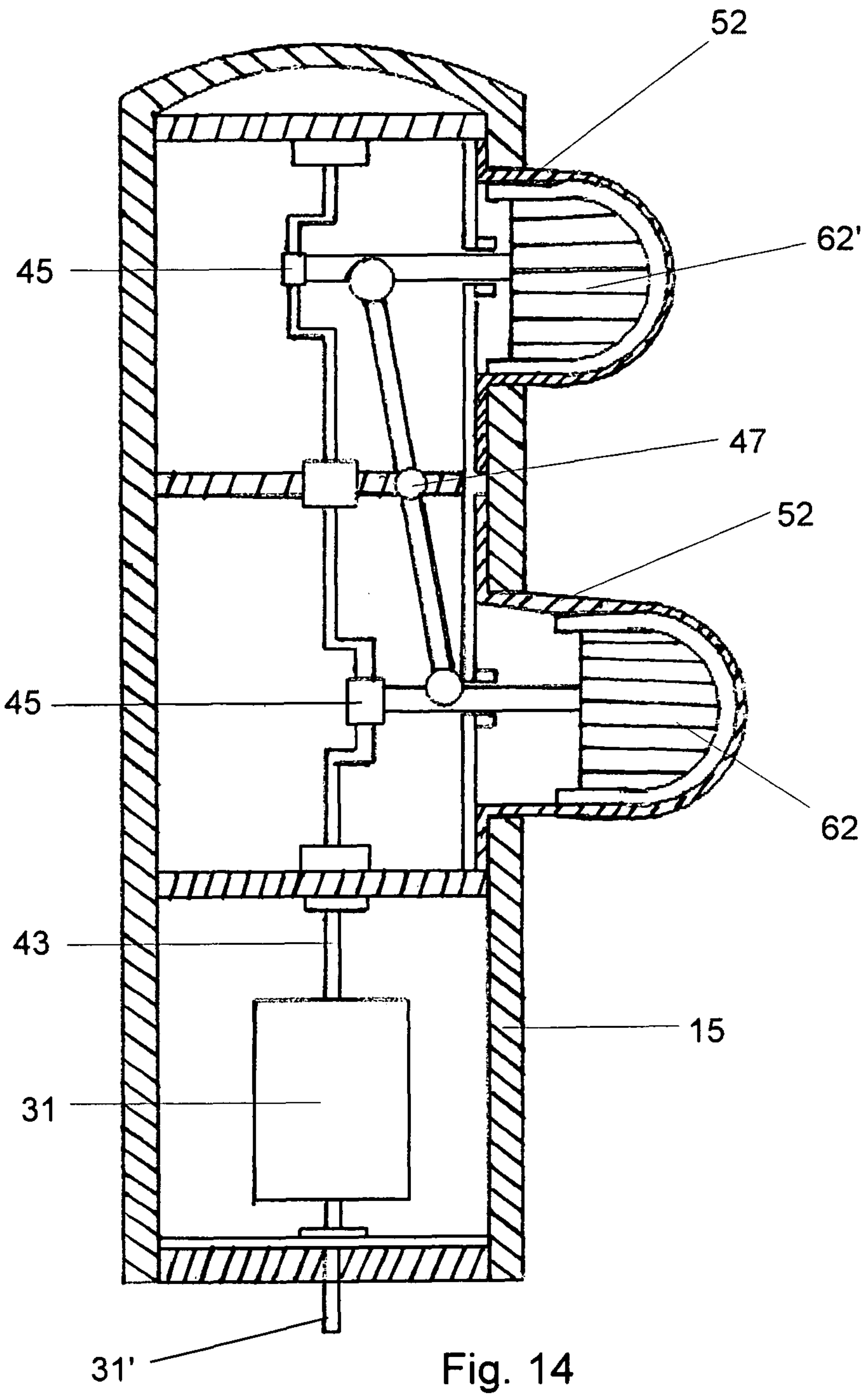
FIG. 14 is a cross sectional view of a basic implementation where the percussive knobs are pneumatically powered in accordance with an embodiment of the present invention.

FIG. 14 is a cross sectional view of a basic implementation where the percussive knobs are pneumatically powered in accordance with an embodiment of the present invention. The embodiment in FIG. 14 comprises a housing 15 with lower 62 and upper 62' massage nodes that are mechanically powered via a pneumatic energy source 31. With this embodiment, the housing could be attached to a handle or a fixed support structure and used underwater.

Figure 15A:
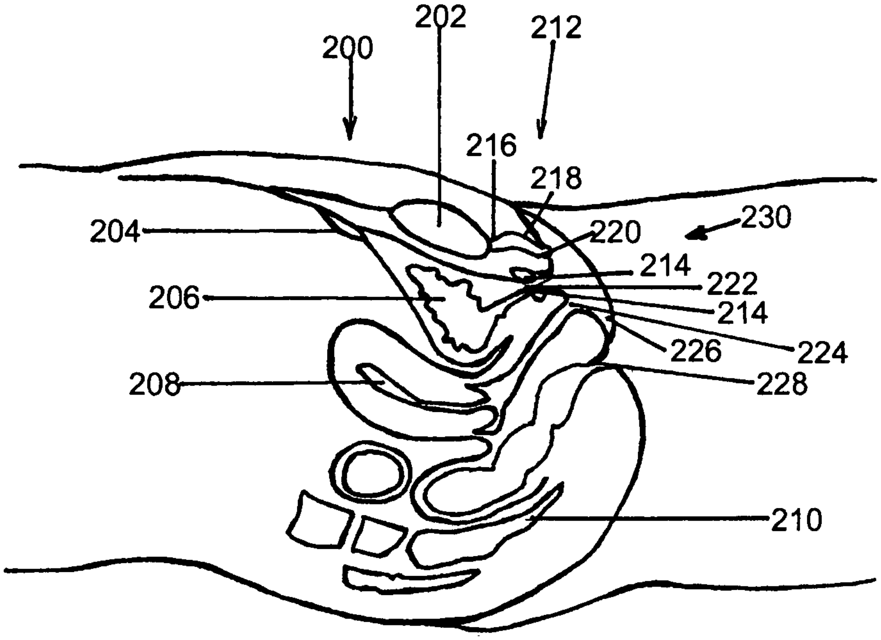
FIG. 15A is a cross sectional view of a woman's lower torso illustrating the structures and tissues that appear to be affected by embodiments of the present invention.

FIG. 15A is a cross sectional view of a woman's lower torso illustrating the structures and tissues that appear to be affected by embodiments of the present invention.

Figure 15B:
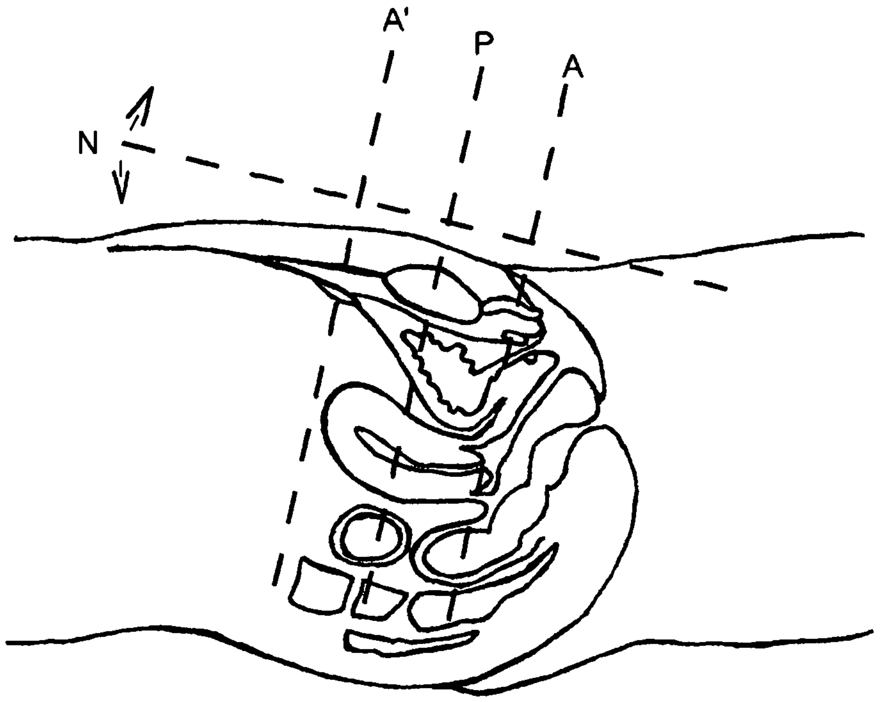
FIG. 15B is a cross sectional view of a woman's lower torso illustrating the correct positioning of the planar and axial lines from embodiments of the present invention.

FIG. 15B is a cross sectional view of a woman's lower torso illustrating the correct positioning of the planar and axial lines from embodiments of the present invention. Once positioned, the planar line N may be adjusted a few degrees towards or away from the woman's pelvis for optimal stimulation.

Figure 15C:
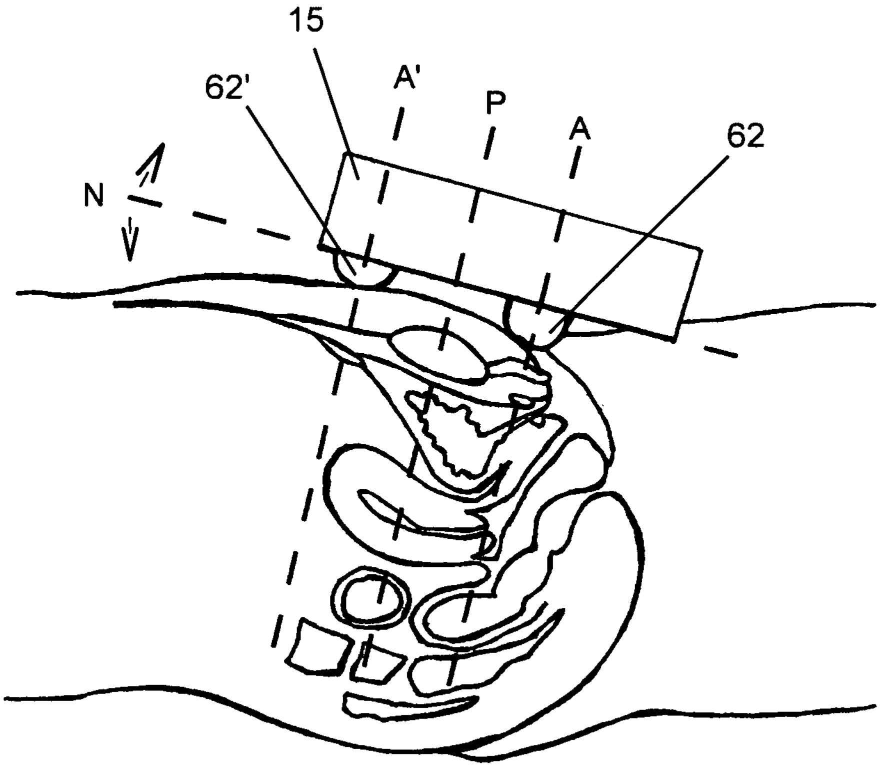
FIG. 15C is a cross sectional view of a woman's lower torso illustrating the correct positioning of a basic implementation in accordance with an embodiment of the present invention.

FIG. 15C is a cross sectional view of a woman's lower torso illustrating the correct positioning of a basic implementation in accordance with an embodiment of the present invention. The correct positioning of the basic embodiment is taken along what would be equivalent to line 2-2 of FIG. 2, represented in dotted lines viewed, positioned in alignment with planar and axial lines for optimal stimulation. Once positioned, the planar line N may be adjusted a few degrees towards or away from the woman's pelvis for optimal stimulation. Massage node 62' is represented as being retracted into the housing 15 and massage node 62 is represented as extended. A supporting structure is not shown.

Figure 15D:
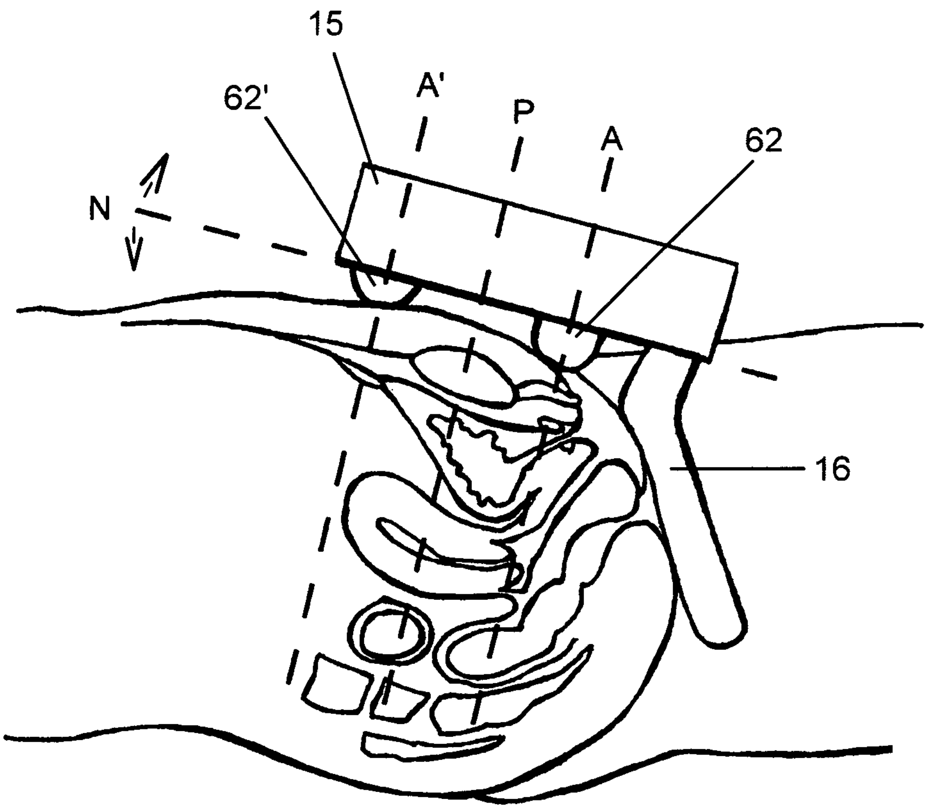
FIG. 15D is a cross sectional view of a woman's lower torso illustrating the correct positioning of a basic implementation in accordance with an embodiment of the present invention that includes a guide.

As shown in FIGS. 15B, 15C, and 15D, the upper percussive massage source 62' is directed into the woman's body in the direction of axis A'. As shown in the same previous drawings, the lower percussive massage source 62 is directed into the woman's body in the direction of axis A. Depending on the woman, and the choice of embodiment used, the planar direction N of the housing 15 may be changed slightly to ensure optimal stimulation of the percussive massage nodes 62' and 62.

As shown in FIG. 15A, stimulation facilitated by the upper percussive massage source 62' appears to affect the tissue in the lower abdomen 200, including the uterine ligament 204, urinary bladder 206, internal aspects of the vagina and aspects of the uterus 208. Further, this percussive stimulation appears to induce vibration of the woman's pubic symphysis 202 (pubic bone and related tissue). Vibration of this structure is transferred via the clitoral suspensory ligament 216 to the body of the clitoris 218, the crura, and glans 220.

Further, in FIG. 15A, at the same time, stimulation facilitated by the lower percussive massage source 62 appears to affect tissue in, and surrounding, the mons pubis region 212. This includes the labia major and minora 230, urethral opening 214 and urethral sphincter muscles 214, the body of the clitoris 218, both legs of the crura connected to the body of the clitoris 218, but not shown, the glans of the clitoris 220, external aspects of the vagina 224, the perineum 226, and anus 228.

Typically, far more intense stimulation can be transferred through the tissue of the mons pubis region 212 than could be directed specifically at the glans of the clitoris 220. However the glans 220 and surrounding regions of the clitoris are all affected at the same time by this regional tissue stimulation. This appears to cause a more mild simulation at the specific site of the clitoris, but the stimulation occurs at all parts simultaneously. This milder simultaneous stimulation appears to produce a profoundly stronger stimulation than just focusing on one point, such as the glans 220.

Stimulation from the lower percussive massage source 62 appears to cause vibration of the entire body of the clitoris 218 and 220. This vibration appears to transfer to the clitoral suspensory ligament 216 and travels upwards to its connection at the pubis symphysis 202. When this vibration traveling upward from the lower massage source 62 combines with stimulation created by the upper massage source 62', which is traveling downward, more intense overall stimulation is typically observed.

As referenced in FIG. 15D, if the option of having a lower vibrational guide is used 16, the woman may elect to engage its vibration during the stimulation of the aforementioned upper and lower massage sources. This vibration can cause stimulation to the lower vaginal region 224, perineum 226, anus 228, coccyx 210 and corresponding base of the spine.

The above sources of stimulation, when combined simultaneously, typically causes profound stimulation of the tissues, resulting in increased blood flow and simultaneous stimulation of both the pelvic and hypogastric nerves. This stimulation typically results in the woman experiencing sexual arousal and orgasm.

Furthermore, the stimulation provided by the upper percussive massage source 62', appears to cause significant vibration to the Uterine Ligament 204. This resulting vibration traveling down the Uterine Ligament 204 appears to cause significant stimulation to both the Uterus and its attachment area to the upper vagina. This vaginal region appears to be very close to where the Gräfenberg Spot (G-Spot) typically is located. Many women using embodiments of the present invention describe a feeling like their G-Spot is being stimulated. It appears vibrational stimulation carried along the uterine ligament 204 may be the cause of this.

Referencing FIG. 15D, the optional vibrational guide 16 is used to assist the woman in easily positioning the upper and lower percussive massage sources, as well as adjusting them to the correct angle for optimal tissue stimulation. As previously mentioned, it can be a source of vibratory stimulation as well. Referencing FIG. 15D, the vibrating guide 16 is shown with the housing 15 positioned where it has been pulled upwards on the woman's axis, causing the vibrating guide to be positioned firmly against the woman's crotch. As a result of the pressure, the vibrating guide flexes slightly, providing contact along the woman's lower pubic area. The upward force of the supporting structure, not shown, combined with the vibrating guide pushing back against that force, particularly if the woman squeezes the vibrating guide 16 with her legs, causes the housing to stay in correct position during operation, thus freeing the woman and or her partner to be able to focus on other aspects of intimacy.

Any of the embodiments of the present invention may be utilized as a method for teaching condom use and safe sex techniques by requiring or suggesting that if the embodiment is shared in public, a covering should be placed over it. This covering should be replaced for each new woman using the embodiment.

The above embodiments and other embodiments, features and advantages of the present invention are more readily understood from a review of the attached drawings and the accompanying specification and claims.

Those skilled in the art will readily recognize, in light of and in accordance with the teachings of the present invention, that any of the foregoing steps may be suitably replaced, reordered, removed and additional steps may be inserted depending upon the needs of the particular application. Moreover, the prescribed method steps of the foregoing embodiments may be implemented using any physical and/or hardware system that those skilled in the art will readily know is suitable in light of the foregoing teachings. For any method steps described in the present application that can be carried out on a computing machine, a typical computer system can, when appropriately configured or designed, serve as a computer system in which those aspects of the invention may be embodied. Such computer system may be comprised of any suitable and common computer hardware, software, middleware, firmware, microcode and the like.

Having fully described at least one embodiment of the present invention, other equivalent or alternative methods of sensual stimulation and orgasm for women according to the present invention will be apparent to those skilled in the art. The invention has been described above by way of illustration, and the specific embodiments disclosed are not intended to limit the invention to the particular forms disclosed. For example, the particular implementation of the drive unit, housing and support structure may vary depending upon the particular type application or environment where the device is used. The embodiments described in the foregoing were directed to electromechanical implementations; however, similar techniques using acoustical vibrations for implementations of the present invention are contemplated as within the scope of the present invention. The invention is thus to cover all modifications, equivalents, and alternatives falling within the spirit and scope of the following claims.

Claim elements and steps herein may have been numbered and/or lettered solely as an aid in readability and understanding. Any such numbering and lettering in itself is not intended to and should not be taken to indicate the ordering of elements and/or steps in the claims.

What is claimed is:

1. An apparatus comprising:

a housing unit;

first means disposed within said housing unit for transferring a first percussive stimulation to a woman's lower abdomen;

second means disposed within said housing unit for transferring, simultaneously with said first percussive stimulation, a second percussive stimulation to the woman's mons pubis region;

means for driving said first means and said second means;

means for supporting said housing unit;

means for adjusting an angle between said housing unit and said supporting means, where said first percussive stimulation and said second percussive stimulation combine to enable the woman to achieve a beneficial stimulation;

means for supporting the apparatus on a floor; and means for adjusting a height of said housing unit above the floor.

2. The apparatus as recited in claim 1, further comprising means for assisting in positioning said first means and said second means.

3. The apparatus as recited in claim 1, further comprising means for at least controlling said driving means where an intensity of said first percussive stimulation and said second percussive stimulation is variable.

4. An apparatus comprising:

a housing unit;

an upper stimulation source disposed within an upper portion of said housing unit, said upper stimulation source being operable for transferring a first percussive stimulation to a woman's lower abdomen proximate a top of a pubic bone;

a lower stimulation source disposed below said upper stimulation source, said lower stimulation source being operable for transferring, simultaneously with said first percussive stimulation, a second percussive stimulation to the woman's mons pubis region proximate a bottom of the pubic bone;

a drive unit disposed within said housing unit for driving said upper stimulation source to generate said first percussive stimulation and said lower stimulation source to generate said second percussive stimulation;

a support unit for supporting said housing unit; and at least one flexible unit for enabling an angle between said housing unit and said support unit to be adjusted, where said first percussive stimulation and said second percussive stimulation combine to enable the woman to achieve a beneficial stimulation.

5. The apparatus as recited in claim 4, further comprising a flexible guide disposed below said lower stimulation source and protruding outward from said housing unit, said flexible guide being operable for assisting in positioning said upper stimulation source and said lower stimulation source.

6. The apparatus as recited in claim 5, in which said flexible guide is further configured to be operable for transferring a vibration to the woman's crotch area.

7. The apparatus as recited in claim 6, further comprising a control unit that is configured to be operable for at least controlling said drive unit where an intensity of said first percussive stimulation and said second percussive stimulation is variable.

8. The apparatus as recited in claim 7, in which said control unit is further configured to be operable for varying an intensity of said vibration.

9. The apparatus as recited in claim 8, further comprising a base unit for supporting the apparatus on a floor, said base unit supporting said support unit.

10. The apparatus as recited in claim 9, further comprising means for adjusting a height of said housing unit above the floor.

11. The apparatus as recited in claim 10, in which said control unit is further configured to be operable for adjusting said height.

12. The apparatus as recited in claim 9, further comprising a second flexible unit for enabling an angle between said base unit and said support unit to be adjusted.

13. The apparatus as recited in claim 9, further comprising a seat.

14. The apparatus as recited in claim 9, in which said base unit comprises a facade.

15. The apparatus as recited in claim 4, in which said drive unit comprises an electric motor.

16. A method comprising:

positioning a housing unit proximate a lower abdomen of a woman where said housing unit comprises an upper stimulation source for generating a first percussive stimulation and a lower stimulation source for generating a second percussive stimulation;

adjusting a height of a supporting unit for said housing unit where said adjusting positions said upper stimulation source to transfer said first percussive stimulation to a location proximate a top of a pubic bone of the woman, and said lower stimulation source to transfer said second percussive stimulation to a location proximate a bottom of the pubic bone;

activating said upper stimulation source to generate said first percussive stimulation and said lower stimulation source to generate said second percussive stimulation; and adjusting an angle between said housing unit and said support unit, where said first percussive stimulation and said second percussive stimulation combine to enable the woman to achieve a beneficial stimulation.

17. The method as recited in claim 16, further comprising using a flexible guide protruding from said housing unit to assist in adjusting said height.

18. The method as recited in claim 17, further comprising activating said flexible guide to generate a vibration.

19. The method as recited in claim 18, further comprising adjusting an intensity of said vibration.

20. The method as recited in claim 16, further comprising adjusting an intensity of said first percussive stimulation and said second percussive stimulation.

* * * * *